(12) United States Patent
Takeuchi et al.

(10) Patent No.: US 10,710,960 B2
(45) Date of Patent: Jul. 14, 2020

(54) CARBON SULFUR MATERIAL AND METHOD FOR PRODUCING SAME

(71) Applicant: National Institute of Advanced Industrial Science and Technology, Tokyo (JP)

(72) Inventors: Tomonari Takeuchi, Osaka (JP); Toshikatsu Kojima, Osaka (JP); Hiroyuki Kageyama, Osaka (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 155 days.

(21) Appl. No.: 15/563,276

(22) PCT Filed: Mar. 24, 2016

(86) PCT No.: PCT/JP2016/059420
§ 371 (c)(1),
(2) Date: Sep. 29, 2017

(87) PCT Pub. No.: WO2016/158675
PCT Pub. Date: Oct. 6, 2016

(65) Prior Publication Data
US 2018/0072665 A1 Mar. 15, 2018

(30) Foreign Application Priority Data

Mar. 31, 2015 (JP) .................................. 2015-073437
Nov. 9, 2015 (JP) .................................. 2015-219767

(51) Int. Cl.
*C07C 381/00* (2006.01)
*C01B 32/70* (2017.01)
(Continued)

(52) U.S. Cl.
CPC ............. *C07C 381/00* (2013.01); *C01B 17/00* (2013.01); *C01B 32/70* (2017.08); *C01B 32/75* (2017.08);
(Continued)

(58) Field of Classification Search
CPC ....... C07C 381/00; C07C 71/02; C01B 17/00; C01B 32/75; C01B 32/70; H01M 4/5815;
(Continued)

(56) References Cited

U.S. PATENT DOCUMENTS

2001/0033971 A1  10/2001  Zhao et al.
2011/0200875 A1  8/2011  Miyuki et al.
(Continued)

FOREIGN PATENT DOCUMENTS

EP  3279141 A1  2/2018
JP  2002/154815 A  5/2002
(Continued)

OTHER PUBLICATIONS

Ji et al "A Highly Ordered Nanostructured Carbon-Sulphur Cathode for Lithium-Sulphur Batteries" Nature Materials vol. 8, pp. 500-506, 2009.
(Continued)

*Primary Examiner* — Gary D Harris
(74) *Attorney, Agent, or Firm* — Cesari and McKenna, LLP

(57) ABSTRACT

The present invention provides an organic sulfur material comprising carbon, hydrogen, and sulfur as constituent elements, and having peaks in the vicinity of 480 cm$^{-1}$, 1250 cm$^{-1}$, 1440 cm$^{-1}$, and 1900 cm$^{-1}$ in a Raman spectrum detected by Raman spectroscopy. The peak in the vicinity of 1440 cm$^{-1}$ is the most intense peak. This organic sulfur material, which is produced by using a liquid organic starting material, achieves high capacity. This organic sulfur
(Continued)

material preferably does not have peaks in the vicinity of 846 cm$^{-1}$ or 1066 cm$^{-1}$.

16 Claims, 12 Drawing Sheets

(51) Int. Cl.
| | | |
|---|---|---|
| H01M 10/052 | (2010.01) | |
| C01B 32/75 | (2017.01) | |
| H01M 4/36 | (2006.01) | |
| H01M 4/62 | (2006.01) | |
| H01M 4/38 | (2006.01) | |
| H01M 4/58 | (2010.01) | |
| C01B 17/00 | (2006.01) | |
| H01M 4/60 | (2006.01) | |
| H01M 10/0562 | (2010.01) | |
| C08L 71/02 | (2006.01) | |
| H01M 10/0525 | (2010.01) | |
| G01N 21/65 | (2006.01) | |

(52) U.S. Cl.
CPC .............. *C08L 71/02* (2013.01); *H01M 4/364* (2013.01); *H01M 4/38* (2013.01); *H01M 4/5815* (2013.01); *H01M 4/60* (2013.01); *H01M 4/625* (2013.01); *H01M 10/052* (2013.01); *H01M 10/0525* (2013.01); *H01M 10/0562* (2013.01); *G01N 21/65* (2013.01); *Y02P 70/54* (2015.11); *Y02T 10/7011* (2013.01)

(58) Field of Classification Search
CPC ........ H01M 4/38; H01M 4/625; H01M 4/364; H01M 10/052; H01M 10/0525; H01M 10/0562; H01M 4/60; C08L 71/02; Y02P 70/54; G02N 21/65; Y02T 10/7011
USPC ........................................................ 429/314
See application file for complete search history.

(56) References Cited

U.S. PATENT DOCUMENTS

| | | | |
|---|---|---|---|
| 2013/0029222 | A1 | 1/2013 | Niwa et al. |
| 2014/0050974 | A1 | 2/2014 | Miyuki et al. |
| 2014/0134485 | A1 | 5/2014 | Miyuki et al. |
| 2016/0293955 | A1 | 10/2016 | Hochi et al. |

FOREIGN PATENT DOCUMENTS

| | | | |
|---|---|---|---|
| JP | 2003/123758 A | | 4/2003 |
| JP | 2011/028948 A | | 2/2011 |
| JP | 2011028948 A | * | 2/2011 |
| JP | 2012/028117 A | | 2/2012 |
| JP | 5142162 B | | 11/2012 |
| JP | 5164286 B | | 12/2012 |
| JP | 2013/084445 A1 | | 6/2013 |
| JP | 2014/096326 A | | 5/2014 |
| JP | 2015/005421 A | | 1/2015 |
| WO | WO-2010/044437 A1 | | 4/2010 |
| WO | WO-2012/132173 A1 | | 10/2012 |
| WO | WO-2012/147242 A1 | | 11/2012 |
| WO | WO-2013/001693 A1 | | 1/2013 |
| WO | WO-2015/050086 A1 | | 4/2015 |

OTHER PUBLICATIONS

Miyuki et al "Section 2.2: Sulfur-Based Cathode" The Latest Technological Trend of Rare Metal-Free Secondary Batteries, Sakai, pp. 81-101, 2013.
Takeuchi et al "Electrochemical Properties of Sulfur-Carbon Composite Positive Electrode Materials Prepared Form Primary Alcohols" The 56$^{th}$ Battery Symposium in Japan, p. 524, 2015.
Trevey et al "Electrochemical Investigation of All-Solid-State Lithium Batteries with a High Capacity Sulfur-Based Electrode" Journal of the Electrochemical Society vol. 159, pp. A1019-A1022, 2012.
Extended Search Report dated Sep. 19, 2018 for European Patent Application No. 16 772 556.3.

* cited by examiner

CARBON SULFUR MATERIAL AND METHOD FOR PRODUCING SAME

CROSS REFERENCE TO RELATED APPLICATIONS

This application is the National Stage of International Application No. PCT/JP2016/059420, filed on Mar. 24, 2016, which claims the benefit of Japanese Application No. 2015-219767, filed on Nov. 9, 2015, and Japanese Application No. 2015-073437, filed on Mar. 31, 2015. The contents of all three applications are hereby incorporated by reference in their entirety.

TECHNICAL FIELD

The present invention relates to an organic sulfur material and a method for producing the organic sulfur material.

BACKGROUND ART

Recent years have seen technical advances in portable electronic devices, hybrid vehicles, etc., and there has been a growing demand for batteries (in particular, secondary batteries, such as lithium-ion secondary batteries) with a higher capacity for use in those devices and vehicles. However, the development of high-capacity cathodes for lithium-ion secondary batteries currently lags behind that of high-capacity anodes. Even actively researched and developed high-capacity Li (Ni,Mn,Co)$O_2$-based materials only have a capacity of about 250 to 300 mAh/g.

Sulfur, which has a theoretical capacity of as high as about 1670 mAh/g and has abundant resources, and which is inexpensive, is one of the promising high-capacity electrode materials. However, elemental sulfur has low conductivity. Further, in battery systems using an organic electrolyte (e.g., lithium-ion secondary batteries), lithium polysulfide generated during the charge and discharge process is dissolved into the electrolyte solution and precipitated on the anode etc., causing the problem of capacity reduction.

To solve this problem, a variety of attempts have been made by forming a composite of elemental sulfur with various organic materials, such as resins and pitch, imparting conductivity to the composite, and inhibiting dissolution and diffusion of lithium polysulfide into the electrolyte solution (e.g., Patent Literature (PTL) 1, PTL 2, and PTL 3, Non-Patent Literature (NPL) 1, NPL 2, and NPL 3). These documents report that the above sulfur-carbon composites exhibit a relatively high capacity and relatively excellent cycle characteristics. Until now, these sulfur-carbon composites have been produced by using, as a starting material of the carbon source, carbon materials, such as porous carbon; polyacrylonitrile (PAN); pitch; or other solid organic substances, and heating the starting material with elemental sulfur or with a sulfur-containing starting material. In particular, an organic sulfur material produced by using PAN as a starting material is considered to be a promising candidate as an electrode material that undergoes less cycle deterioration.

CITATION LIST

Patent Literature

PTL 1: JP5164286B
PTL 2: JP5142162B
PTL 3: WO 2010/044437

Non-Patent Literature

NPL 1: The Latest Technological Trend of Rare Metal-Free Secondary Batteries, supervised by Tetsuo Sakai, CMC Publishing Co., Ltd. (2013).
NPL 2: X. Ji et al., Nat. Mater., 8, and 500 (2009).
NPL 3: J. E. Trevey et al., J. Electrochem. Soc., 159, A1019 (2012).

SUMMARY OF INVENTION

Technical Problem

In terms of material synthesis, substances diffuse slowly in a reaction that uses a solid material, compared to liquid or gaseous systems, and the reaction is thus likely to proceed more slowly than in liquid or gaseous systems. To allow the reaction to efficiently proceed, it is preferable to use a method for, for example, liquefying or vaporizing the solid material, or to use a liquid or gaseous material. Liquefaction or vaporization of a solid material requires a remarkably high temperature, which is disadvantageous from the viewpoint of the manufacturing costs and the processes. Thus, performing a reaction using a liquid or gaseous material is a realistic approach; however, the use of an organic starting material in a liquid or gaseous form to produce an organic sulfur material in this manner has not even been considered.

The present invention has been made in view of the current status of the related art described above. The main object is to provide an organic sulfur material with a high capacity by using an organic starting material in a liquid form.

Solution to Problem

The present inventors conducted extensive research to achieve the above object and found that subjecting a solution containing a sulfur-containing starting material and a linear or branched alcohol, a linear or branched carboxylic acid, a linear or branched aldehyde, or the like to heat treatment in an inert atmosphere allows the high-temperature alcohol, carboxylic acid, aldehyde, or the like (liquid) to be brought into contact with the sulfur-containing starting material to thus allow a reaction to proceed, which makes it possible to yield an organic sulfur material in which the liquid organic substance that has undergone carbonization and thus has conductivity is efficiently bonded to sulfur. The thus-obtained organic sulfur material has characteristic peaks in a Raman spectrum. The present invention has been accomplished through further research based on the above findings. Specifically, the present invention encompasses the following.

Item 1. An organic sulfur material comprising carbon, hydrogen, and sulfur as constituent elements, and having peaks in the vicinity of 480 $cm^{-1}$, 1250 $cm^{-1}$, 1440 $cm^{-1}$, and 1900 $cm^{-1}$ in a Raman spectrum detected by Raman spectroscopy, the peak in the vicinity of 1440 $cm^{-1}$ being most intense.

Item 2. The organic sulfur material according to Item 1, wherein the Raman scattering peak intensity in the vicinity of 480 $cm^{-1}$, the Raman scattering peak intensity in the vicinity of 1250 $cm^{-1}$, and the Raman scattering peak intensity in the vicinity of 1900 $cm^{-1}$ are all 0.5 times, or less, the Raman scattering peak intensity in the vicinity of 1440 $cm^{-1}$.

Item 3. The organic sulfur material according to Item 1 or 2, having no peak of Raman scattering intensity in the vicinity of 846 cm$^{-1}$ or 1066 cm$^{-1}$ in the Raman spectrum detected by Raman spectroscopy.

Item 4. The organic sulfur material according to any one of Items 1 to 3, wherein the population of a component having a peak of Raman scattering intensity in the vicinity of 1440 cm$^{-1}$ is 50% or more when fitting is performed with respect to four components, each having a peak of Raman scattering intensity in the vicinity of 1270 cm$^{-1}$, 1350 cm$^{-1}$, 1440 cm$^{-1}$, or 1590 cm$^{-1}$ in the Raman spectrum within a range of 1000 to 2000 cm$^{-1}$ detected by Raman spectroscopy.

Item 5. The organic sulfur material according to any one of Items 1 to 4, having peaks in the vicinity of 2469 eV, 2472 eV, and 2473 eV in an S K-edge X-ray absorption fine structure spectrum, the peak in the vicinity of 2473 eV being most intense.

Item 6. The organic sulfur material according to any one of Items 1 to 5, wherein the carbon content is 30 to 45 wt %, the sulfur content is 55 to 70 wt %, the hydrogen content is 1 wt % or less, the oxygen content is 1 wt % or less, and the nitrogen content is 1 wt % or less.

Item 7. A method for producing an organic sulfur material comprising carbon, hydrogen, and sulfur as constituent elements, and having peaks in the vicinity of 480 cm$^{-1}$, 1250 cm$^{-1}$, 1440 cm$^{-1}$, and 1900 cm$^{-1}$ in a Raman spectrum detected by Raman spectroscopy, the peak in the vicinity of 1440 cm$^{-1}$ being most intense, the method comprising the step of subjecting a solution containing a sulfur-containing starting material and at least one member selected from the group consisting of linear or branched alcohols, linear or branched carboxylic acids, and linear or branched aldehydes to heat treatment in an inert atmosphere.

Item 8. The production method according to Item 7, wherein the heat treatment step comprises refluxing at 300 to 600° C. the solution containing a sulfur-containing starting material and at least one member selected from the group consisting of linear or branched alcohols, linear or branched carboxylic acids, and linear or branched aldehydes.

Item 9. The production method according to Item 7 or 8, wherein the method comprises the step of performing heating at 250 to 350° C. under an inert gas stream after the heat treatment step.

Item 10. An electrode active material for a battery, the material comprising the organic sulfur material of any one of Items 1 to 6.

Item 11. An electrode active material for a battery, the material comprising the organic sulfur material obtained by the production method of any one of Items 7 to 9.

Item 12. The electrode active material for a battery according to Item 10 or 11, which is an electrode active material for a lithium-ion secondary battery.

Item 13. A battery comprising, as a constituent element, the electrode active material for a battery of any one of Items 10 to 12.

Item 14. The battery according to Item 13, which is a lithium-ion secondary battery.

Item 15. An all-solid-state lithium-ion secondary battery comprising, as constituent elements, the electrode active material for a battery of any one of Items 10 to 12, and a lithium-ion conductive solid electrolyte.

Item 16. The all-solid-state lithium-ion secondary battery according to Item 15, wherein the lithium-ion conductive solid electrolyte contains an inorganic compound containing sulfur as a constituent element.

Advantageous Effects of Invention

In the organic sulfur material of the present invention, a carbide obtained by calcining an organic substance is amorphous and has a relatively high conductivity; the sulfur is trapped within the carbide pores, and is thus unlikely to vaporize even at a temperature as high as 400° C., which can inhibit dissolution and diffusion of sulfur released as lithium polysulfide at the time of lithium insertion and extraction during charge and discharge, into the electrolyte solution. For this reason, the organic sulfur material of the present invention exhibits excellent charge-discharge characteristics (in particular, high capacity). Moreover, the organic sulfur material of the present invention may also possibly exhibit excellent cycle characteristics.

Accordingly, the organic sulfur material of the present invention is useful as an electrode active material (in particular, as a cathode active material) for a battery, such as a lithium-ion secondary battery, and is applicable to both a non-aqueous electrolyte lithium-ion secondary battery and an all-solid-state lithium-ion secondary battery.

The production method of the present invention is capable of producing an organic sulfur material that exhibits excellent performance described above by using an inexpensive, general-purpose liquid organic starting material, which has never been reported before.

DESCRIPTION OF EMBODIMENTS

1. Organic Sulfur Material

Figure 1:
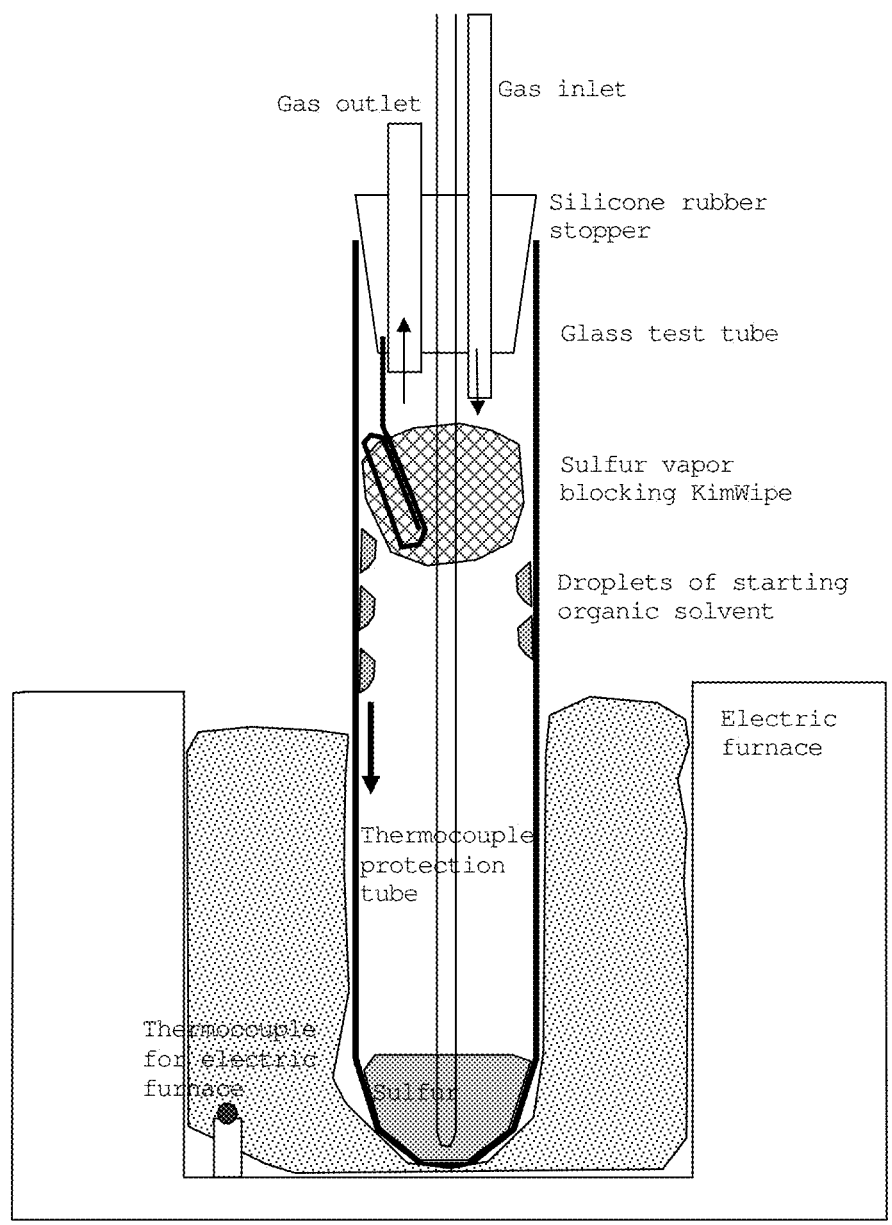
FIG. 1 is a cross-sectional schematic view showing one example of the device used in the production method of the present invention.

The organic sulfur material of the present invention comprises carbon, hydrogen, and sulfur as constituent elements, and has peaks in the vicinity of 480 cm$^{-1}$, 1250 cm$^{-1}$, 1440 cm$^{-1}$, and 1900 cm$^{-1}$ in a Raman spectrum detected by Raman spectroscopy. The peak in the vicinity of 1440 cm$^{-1}$ is the most intense peak.

In the organic sulfur material of the present invention, sulfur is trapped within a carbide originating form a starting material. The carbide originating form a starting material is amorphous and has a relatively high conductivity. In the organic sulfur material of the present invention, the sulfur is presumably confined within a carbide skeleton formed from carbon atoms originating from an alcoholic skeleton, a carboxylic acid skeleton, an aldehyde skeleton, or the like, making it possible to reduce unreacted sulfur (free sulfur) and thus inhibit dissolution and diffusion of sulfur released as lithium polysulfide at the time of lithium insertion and extraction during charge and discharge, into the electrolyte solution. For this reason, the organic sulfur material of the present invention exhibits excellent charge-discharge characteristics (high capacity and excellent cycle characteristics).

The organic sulfur material of the present invention comprises carbon, hydrogen, and sulfur as constituent elements.

The content of each element in the organic sulfur material of the present invention is not particularly limited. For example, the carbon content may be adjusted to 30 to 45 wt % (in particular 32 to 40 wt %), the sulfur content may be adjusted to 55 to 70 wt % (in particular 57 to 67 wt %), the hydrogen content may be adjusted to 1 wt % or less (in particular 0.01 to 0.7 wt %), the oxygen content may be adjusted to 1 wt % or less (in particular 0.01 to 0.5 wt %), and the nitrogen content may be adjusted to 1 wt % or less (in particular 0.01 to 0.5 wt %). In this manner, it is possible to achieve more excellent charge-discharge characteristics (in particular, high capacity), as well as more excellent cycle characteristics. The content of each constituent element in the organic sulfur material of the present invention is measured by using a combustion method.

In addition to carbon, hydrogen, and sulfur, the organic sulfur material of the present invention may contain a small amount of heteroatoms, such as nitrogen, oxygen, and phosphorus, to an extent that the effects of the present invention are not impaired. If the content is 10 wt % or less, in particular 0.01 to 5 wt %, these heteroatoms have a limited impact on the charge-discharge characteristics.

The organic sulfur material of the present invention has peaks in the vicinity of 480 cm$^{-1}$, 1250 cm$^{-1}$, 1440 cm$^{-1}$, and 1900 cm$^{-1}$ in a Raman spectrum detected by Raman spectroscopy, and the peak in the vicinity of 1440 cm$^{-1}$ is the most intense peak.

The organic sulfur material of the present invention has an S—S bond, and thus has a peak in the vicinity of 480 cm$^{-1}$, which represents the S—S bond stretching vibration. This peak position has a tolerance of ±50 cm$^{-1}$, in particular ±30 cm$^{-1}$. Specifically, the organic sulfur material of the present invention has a peak between 430 and 530 cm$^{-1}$, in particular between 450 and 510 cm$^{-1}$.

The organic sulfur material of the present invention has a carbon skeleton (C—C bond) of carbide originating from an alcohol, carboxylic acid, or aldehyde, and thus has a peak in the vicinity of 1250 cm$^{-1}$, which represents the D-band. This peak position has a tolerance of ±50 cm$^{-1}$, in particular ±30 cm$^{-1}$. Specifically, the organic sulfur material of the present invention has a peak between 1200 and 1300 cm$^{-1}$, in particular between 1220 and 1280 cm$^{-1}$.

The organic sulfur material of the present invention has a carbon skeleton (C—C bond) of carbide originating from an alcohol, carboxylic acid, or aldehyde, and thus has a peak in the vicinity of 1440 cm$^{-1}$, which represents the G-band. This peak position has a tolerance of ±50 cm$^{-1}$, in particular ±30 cm$^{-1}$. Specifically, the organic sulfur material of the present invention has a peak between 1390 and 1490 cm$^{-1}$, in particular between 1410 and 1470 cm$^{-1}$.

The organic sulfur material of the present invention has a C—H bond, and thus has a peak in the vicinity of 1900 cm$^{-1}$, which represents the deformation vibration. This peak position has a tolerance of ±50 cm$^{-1}$, in particular ±30 cm$^{-1}$. Specifically, the organic sulfur material of the present invention has a peak between 1850 and 1950 cm$^{-1}$, in particular between 1870 and 1930 cm$^1$.

In the organic sulfur material of the present invention, the peak in the vicinity of 1440 cm$^{-1}$ is the most intense peak among these four different peaks. Therefore, there is a large amount of the sp$^3$ component of the G-band, and the majority of carbon components form an undeveloped graphene skeleton. That is, a carbon skeleton with relatively high conductivity and structure flexibility is formed, which allows the organic sulfur material of the present invention to serve as an electrode material that can withstand the expansion and shrinkage caused by charge and discharge. In this specification, "the most intense peak" refers to a peak with the highest peak intensity. In particular, the Raman scattering peak intensity in the vicinity of 480 cm$^{-1}$, the Raman scattering peak intensity in the vicinity of 1250 cm$^{-1}$, and the Raman scattering peak intensity in the vicinity of 1900 cm$^{-1}$ are all 0.5 times, or less, and preferably 0.01 to 0.4 times, the Raman scattering peak intensity in the vicinity of 1440 cm$^{-1}$. If sulfur is treated with resin (e.g., PAN), pitch, or the like as is conventionally done, two intense peaks would be likely to appear in the vicinity of 1435 cm$^{-1}$ and 1530 cm$^{-1}$, and the most intense peak in the vicinity of 1440 cm$^{-1}$ would not appear.

The organic sulfur material of the present invention, which has the four different peaks in the Raman spectrum detected by Raman spectroscopy, preferably does not have peaks in the vicinity of 846 cm$^{-1}$ or 1066 cm$^{-1}$. These positions have a tolerance of ±50 cm$^{-1}$, in particular ±30 cm$^{-1}$. Specifically, the organic sulfur material of the present invention preferably does not have peaks between 796 and 896 cm$^{-1}$ or between 1016 and 1116 cm$^{-1}$, in particular between 816 and 876 cm$^{-1}$ or between 1036 and 1096 cm$^{-1}$.

The organic sulfur material of the present invention preferably comprises a highly conductive carbide to further improve conductivity, and comprises a component having an S—C bond to further reduce free sulfur. The highly conductive carbide is mainly composed of carbon. When this highly conductive carbide is produced, for example, by the production method described later, the properties of the skeleton portion (alkane skeleton) of a linear or branched hydrocarbon of a starting material such as a linear or branched alcohol, a linear or branched carboxylic acid, and a linear or branched aldehyde would remain while fused polycycles are assembled. Thus, the Raman spectrum detected by Raman spectroscopy preferably shows the presence of a large amount of $sp^3$ component of the G band.

In the present invention, whether the $sp^3$ component of the G band is contained in a large amount is determined by the method disclosed in M. M. Doeff et al., Electrochem. Solid-State Lett., 6, A207 (2003). More specifically, the population of the $sp^3$ component of the G band (1440 cm$^{-1}$) is preferably 50% or more (50 to 100%), and more preferably 60 to 99.99%, when fitting is performed with respect to the $sp^3$ component of the D band (1270 cm$^{-1}$), the $sp^2$ component of the D band (1350 cm$^{-1}$), the $sp^3$ component of the G band (1440 cm$^1$), and the $sp^2$ component of the of G band (1590 cm$^{-1}$). If sulfur is treated with resin (e.g., PAN), pitch, or the like as is conventionally done, intense peaks of the $sp^2$ component of the D band (1350 cm$^{-1}$) and the $sp^2$ component of the G band (1590 cm$^{-1}$) would be likely to appear, and the population of the $sp^3$ component of the G band (1440 cm$^{-1}$) would be significantly small.

The X-ray absorption fine structure (XAFS) spectrum is an absorption spectrum obtained upon excitation of inner shell electrons by irradiation with X-rays, and gives information on each target element. The organic sulfur material of the present invention has peaks in the vicinity of 2469 eV, 2472 eV, and 2473 eV in an S K-edge X-ray absorption fine structure spectrum, and the peak in the vicinity of 2473 eV is preferably the most intense peak.

The organic sulfur material of the present invention preferably has a peak in the vicinity of 2469 eV, which suggests a transition from $S^{2-}$ or $S_2^{2-}$ that forms hybrid-orbitals with a graphene skeleton structure. This peak position has a tolerance of ±0.5 eV, in particular ±0.3 eV. Specifically, the organic sulfur material of the present invention preferably has a peak between 2468.5 and 2469.5 eV, in particular between 2468.7 and 2469.3 eV.

The organic sulfur material of the present invention preferably has a peak in the vicinity of 2472 eV, which suggests a transition inside an isolated sulfur atom or inside sulfur bonding to sulfur at both ends (—S—S—S—). This peak position has a tolerance of ±0.5 eV, in particular ±0.3 eV. Specifically, the organic sulfur material of the present invention preferably has a peak between 2471.5 and 2472.5 eV, in particular between 2471.7 and 2472.3 eV.

The organic sulfur material of the present invention has an S—R bond (R is an alkyl group), and preferably has a peak in the vicinity of 2473 eV, which suggests a transition from hybrid-orbitals of C or H in the alkyl group with S. This peak position has a tolerance of ±0.5 eV, in particular ±0.3 eV. Specifically, the organic sulfur material of the present invention preferably has a peak between 2472.5 and 2473.5 eV, in particular between 2472.7 and 2473.3 eV.

In the organic sulfur material of the present invention, the peak in the vicinity of 2473 eV is preferably the most intense peak among these three different peaks. In this case, the presence of an S—R bond is notably indicated. In particular, both the XAFS peak intensity in the vicinity of 2469 eV and the XAFS peak intensity in the vicinity of 2472 eV are preferably 0.8 times, or less, more preferably 0.01 to 0.7 times, or less, the XAFS peak intensity in the vicinity of 2473 eV. However, if sulfur is treated with resin (e.g., PAN), pitch, or the like as is conventionally done, an intense peak in the vicinity of 2471.7 eV would be likely to appear while the most intense peak would not appear in the vicinity of 2473 eV.

Although the organic sulfur material of the present invention satisfies the above requirements, other impurities may optionally be incorporated as long as the performance of the organic sulfur material is not impaired. Examples of the impurities include nitrogen, oxygen, and the like, that can be incorporated into the starting materials or during the production.

Additionally, a starting material residue (e.g., alcohol, carboxylic acid, aldehyde, and sulfur), a reaction product that is not a target product of the present invention, and the like may also be incorporated as impurities. The amount of these impurities is not limited as long as the above performance of the organic sulfur material is not impaired, and is preferably 10 wt % or less, more preferably 5 wt % or less, and still more preferably 0.01 to 3 wt % or less, taking the total amount of the organic sulfur compound, which satisfies the above requirements, as 100 wt %.

2. Production Method of Organic Sulfur Material

Without limiting the present invention, the organic sulfur material of the present invention may be obtained by using a production method comprising the step of subjecting a solution containing a sulfur-containing starting material, and a linear or branched alcohol, a linear or branched carboxylic acid, a linear or branched aldehyde, or the like to heat treatment in an inert atmosphere. The heat treatment is preferably performed, in particular, by using a reflux method, which comprises performing refluxing. According to this method, it is possible to obtain an organic sulfur material in which the linear or branched alcohol, linear or branched carboxylic acid, linear or branched aldehyde, or the like that has undergone carbonization is bonded, while having conductivity, to the sulfur-containing starting material, and in which generation of free sulfur is suppressed. For the starting materials, it is possible to use linear or branched alcohols, linear or branched carboxylic acids, and linear or branched aldehydes in combination. The following more specifically describes this method.

(2-1) Starting Compound

In the present invention, a sulfur-containing starting material, a linear or branched alcohol, a linear or branched carboxylic acid, a linear or branched aldehyde, and the like are used as starting materials.

The sulfur-containing starting material is not particularly limited, and may contain, in addition to a sulfur element, elements that are to be released and volatilized during heat treatment (e.g., carbon, hydrogen, nitrogen, and oxygen). However, the sulfur-containing starting material preferably contains no metal element. Examples of the sulfur-containing starting material include sulfur (S) and the like. The sulfur-containing starting material may be used alone or in a combination of two or more.

The form of the sulfur-containing starting material is not particularly limited, and may be a solid or a liquid. As a solid, a powder with an average particle size of about 0.1 to 100 μm is preferable. The average particle size of the starting material compound is determined as the value at which the cumulative population reaches 50% in particle size distribution measured by using a dry laser diffraction/scattering method. It is possible to use starting material compounds having a large particle size, and adjust the average particle size by pulverizing the materials using a mortar or the like.

The linear or branched alcohol is not particularly limited and preferably efficiently undergoes carbonization in the process of producing the organic sulfur material to thus serve as a component that enhances conductivity; thus, the number of carbon atoms (n(C)) is preferably in excess, exceeding about 3 times the number of oxygen atoms (n(O)), i.e., n(C)>3n(O). In general, n(O)=1 in a linear or branched alcohol; thus, n(C)>3 is preferable. That is, the carbon number of the linear or branched alcohol is preferably an integer of 4 or more, and in particular an integer of 6 or more. The upper limit of the carbon number of linear or branched alcohol may be arbitrarily selected based on those that are in a liquid form at the reaction temperature; however, in the organic sulfur compound, the amount of carbon, which is not involved in charge and discharge, is preferably adjusted to be as small as possible to achieve a high capacity. Therefore, the carbon number of linear or branched alcohol is preferably an integer of 12 or less, and more preferably an integer of 10 or less.

Of linear alcohols and branched alcohols, it is preferable to use linear alcohols. This is because linear alcohols relatively easily undergo carbonization, and the resulting carbides have a relatively high conductivity, which makes it possible to enhance the utilization of the active material and to achieve a high capacity.

Specific examples of the linear or branched alcohol include 1-butanol, 1-pentanol, 1-hexanol, 1-heptanol, 1-octanol, 1-nonanol, 1-decanol, and the like. These linear or branched alcohols may be used alone or in a combination of two or more.

The linear or branched carboxylic acid is not particularly limited and preferably efficiently undergoes carbonization in the process of producing the organic sulfur material to thus serve as a component that enhances conductivity; thus, the number of carbon atoms (n(C)) in the alkyl-group moiety is preferably the same as in the linear alcohols and branched alcohols. That is, the carbon number of the alkyl-group moiety in the linear or branched carboxylic acid is preferably an integer of 4 or more, and in particular an integer of 6 or more. Similarly, the carbon number of the linear or branched carboxylic acid is preferably an integer of 5 or more, and in particular an integer of 7 or more. The upper limit of the carbon number of the alkyl-group moiety in the linear or branched carboxylic acid may be arbitrarily selected based on those that are in a liquid form at the reaction temperature; however, in the organic sulfur compound, the amount of carbon, which is not involved in charge and discharge, is preferably adjusted to be as small as possible to achieve a high capacity. Therefore, the carbon number of the alkyl-group moiety in the linear or branched carboxylic acid is preferably an integer of 12 or less, and more preferably an integer of 10 or less. Similarly, the upper limit of the carbon number of the linear or branched carboxylic acid is preferably an integer of 13 or less, and in particular an integer of 11 or less.

Of linear carboxylic acids and branched carboxylic acids, it is preferable to use linear carboxylic acids. This is because linear carboxylic acids relatively easily undergo carbonization, and the resulting carbides have a relatively high conductivity, which makes it possible to enhance the utilization of the active material and to achieve a high capacity.

Specific example of the linear or branched carboxylic acid include 1-butanoic acid, 1-pentanoic acid, 1-hexanoic acid, 1-heptanoic acid, 1-octanoic acid, 1-nonanoic acid, 1-decanoic acid, and the like. These linear or branched carboxylic acids may be used alone or in a combination of two or more.

The linear or branched linear or branched aldehyde is not particularly limited and preferably efficiently undergoes carbonization in the process of producing the organic sulfur material to thus serve as a component that enhances conductivity; thus, the number of carbon atoms (n(C)) in the alkyl-group moiety is preferably the same as in the linear alcohols and branched alcohols. That is, the carbon number of the alkyl-group moiety in the linear or branched aldehyde is preferably an integer of 4 or more, and in particular an integer of 6 or more. Similarly, the carbon number of the linear or branched aldehyde is preferably an integer of 5 or more, and in particular an integer of 7 or more. The upper limit of the carbon number of the alkyl-group moiety in the linear or branched aldehyde may be arbitrarily selected based on those that are in a liquid form at the reaction temperature; however, in the organic sulfur compound, the amount of carbon, which is not involved in charge and discharge, is preferably adjusted to be as small as possible to achieve a high capacity. Therefore, the carbon number of the alkyl-group moiety in the linear or branched aldehyde is preferably an integer of 12 or less, and more preferably an integer of 10 or less. Similarly, the upper limit of the carbon number of the linear or branched aldehyde is preferably an integer of 13 or less, and in particular an integer of 11 or less.

Of linear aldehydes and branched aldehydes, it is preferable to use linear aldehydes. This is because linear aldehydes relatively easily undergo carbonization, and the resulting carbides have a relatively high conductivity, which makes it possible to enhance the utilization of the active material and to achieve a high capacity.

Specific examples of the linear or branched aldehyde include 1-butyraldehyde (butanal), 1-valeraldehyde (pentanal), 1-hexylaldehyde (hexanal), 1-heptaldehyde (heptanal), 1-octaldehyde (octanal), 1-nonylaldehyde (nonanal), 1-decylaldehyde (decanal), and the like. These linear or branched aldehydes may be used alone or in a combination of two or more.

These linear or branched alcohols, linear or branched carboxylic acids, linear or branched aldehydes, and the like may be used alone or in a combination of two or more.

The mixing ratio of the sulfur-containing starting material to the linear or branched alcohol, linear or branched carboxylic acid, linear or branched aldehyde, or the like is not particularly limited. Considering that the sulfur component turns into hydrogen sulfide ($H_2S$) and vaporizes during the reaction process, and considering that any residue of the sulfur-containing starting material can be removed in the heating step mentioned later, it is preferable that the sulfur-containing starting material be excessively contained, relative to the linear or branched alcohol, linear or branched carboxylic acid, linear or branched aldehyde, or the like. The amount used of the linear or branched alcohol, linear or branched carboxylic acid, linear or branched aldehyde, or the like is preferably adjusted in such a manner that the final product, i.e., the organic sulfur material, contains carbon (produced by carbonization of linear or branched alcohol, linear or branched carboxylic acid, linear or branched aldehyde, or the like), to an extent that sufficient conductivity is achieved. From this viewpoint, the amount used of the linear or branched alcohol, linear or branched carboxylic acid, linear or branched aldehyde, or the like is preferably 20 to 60 parts by weight, and more preferably 30 to 50 parts by weight, per 100 parts by weight of the sulfur-containing starting material, although it depends on, for example, the carbon number of the linear or branched alcohol, linear or branched carboxylic acid, linear or branched aldehyde, or the like, as well as the amount of sulfur contained in the sulfur-containing starting material. When two or more members are used in combination from among the linear or branched alcohols, linear or branched carboxylic acids, linear or branched aldehydes, and the like, the total amount is preferably adjusted to be within the above range.

In the present invention, in addition to the starting materials above, it is also possible to additionally use a nitrogen atom-containing compound, which is compatible with a sulfur atom. Examples of the usable nitrogen atom-containing compound include hydrazine and the like.

In the present invention, the starting material comprising a sulfur-containing starting material and a linear or branched alcohol, a linear or branched carboxylic acid, a linear or branched aldehyde, or the like is preferably used in a solution form at a reaction temperature (300° C. or higher). The linear or branched alcohols, linear or branched carboxylic acids, linear or branched aldehydes, and the like, that satisfy the above requirement are usually a liquid; thus, when a sulfur-containing starting material is mixed with a linear or branched alcohol, a linear or branched carboxylic acid, a linear or branched aldehyde, or the like, a solution is obtained containing the sulfur-containing starting material and the linear or branched alcohol, linear or branched carboxylic acid, linear or branched aldehyde, or the like. The linear or branched alcohol, linear or branched carboxylic acid, linear or branched aldehyde, or the like is to be used as a liquid; thus, a compound that is in a liquid form at 300° C. is preferable.

(2-2) Production Method of Organic Sulfur Material

In the production method of the present invention, the starting compounds described above are used. Specifically, a solution containing a sulfur-containing starting material, and a linear or branched alcohol, a linear or branched carboxylic acid, a linear or branched aldehyde, or the like is subjected to heat treatment in an inert atmosphere. In the present invention, a solution containing a sulfur-containing starting material, and a linear or branched alcohol, a linear or branched carboxylic acid, a linear or branched aldehyde, or the like is preferably refluxed at 300° C. or higher.

For example, as shown in FIG. 1, in the heat treatment performed by a reflux method, the starting material (a solution containing a sulfur-containing starting material, and a linear or branched alcohol, a linear or branched carboxylic acid, a linear or branched aldehyde, or the like) is placed in a reactor (e.g., a test tube), and the upper part of the reactor is preferably cooled while the lower part of the reactor is heated in an electric furnace or the like. At this time, the reactor is preferably semi-sealed. In this process, the sulfur-containing starting material melts at the bottom of the reactor and reacts with the heated linear or branched alcohol, linear or branched carboxylic acid, linear or branched aldehyde, or the like; and at the same time, the linear or branched alcohol, linear or branched carboxylic acid, linear or branched aldehyde, or the like itself undergoes carbonization. The heated starting materials (the sulfur-containing starting material, and the linear or branched alcohol, linear or branched carboxylic acid, linear or branched aldehyde, or the like) and a reaction intermediate partly vaporize once and return as reflux to the reaction system. As this process is repeated, the starting materials (the sulfur-containing starting material, and the linear or branched alcohol, linear or branched carboxylic acid, linear or branched aldehyde, or the like) actively undergo a reaction, allowing the reaction to proceed efficiently. In this reaction process, carbonization of the linear or branched alcohol, linear or branched carboxylic acid, linear or branched aldehyde, or the like presumably proceeds due to dehydration and/or dehydrogenation, and at the same time, sulfur is incorporated into the carbide. At this time, the yield is easily improved if the linear or branched alcohol, linear or branched carboxylic acid, linear or branched aldehyde, or the like in a liquid form is added little by little to a reactor (e.g., a test tube) that contains the sulfur-containing starting material.

In this reflux method, the inert atmosphere is not particularly limited, and may be a nitrogen gas atmosphere, an argon gas atmosphere, or the like.

The reaction temperature and retention time in this reflux method are not particularly limited. Although it depends on the melting point, boiling point, etc., of the starting materials (a sulfur-containing starting material, and a linear or branched alcohol, a linear or branched carboxylic acid, a linear or branched aldehyde, or the like), the reaction temperature is usually 300° C. or higher, preferably 350 to 600° C., and more preferably 380 to 500° C., and the retention time is usually 5 to 100 minutes, preferably 10 to 60 minutes, and more preferably 20 to 40 minutes. A reaction temperature within the above range allows each starting material to more sufficiently undergo a reaction, and allows the linear or branched alcohol, linear or branched carboxylic acid, linear or branched aldehyde, or the like to more sufficiently undergo carbonization and to more sufficiently form a bond with the sulfur-containing starting material, which makes it possible to further reduce unreacted sulfur (free sulfur) and achieve higher capacity. Further, a retention time within the above range allows each starting material to more sufficiently undergo a reaction and allows the linear or branched alcohol, linear or branched carboxylic acid, linear or branched aldehyde, or the like to more sufficiently undergo carbonization and to more sufficiently form a bond with the sulfur-containing starting material, which makes it possible to further reduce unreacted sulfur (free sulfur) and achieve higher capacity, and which, at the same time, makes it possible to further suppress volatilization of the linear or branched alcohol, linear or branched carboxylic acid, linear or branched aldehyde, or the like with the sulfur-containing starting material and to more improve the yield of the reaction product. In the present invention, "retention time" refers to a retention time at the maximum temperature.

When the reflux reaction is performed in the above manner, it is possible to obtain the organic sulfur material of the present invention described above while reducing free sulfur remaining unreacted, although free sulfur may sometimes be contained. In this case, the free sulfur remaining unreacted is preferably vaporized and/or removed by heating the reaction product at 250 to 350° C. under an inert gas stream. In this manner, free sulfur is more reliably removed, enabling a further improvement of the conductivity and capacity. If free sulfur remains in the organic sulfur compound, the conductivity of the organic sulfur compound is reduced, and when charge and discharge are repeated in a battery system using an organic electrolyte solution, the sulfur is dissolved and diffused as lithium polysulfide in the electrolyte solution, causing a reduction in the capacity.

The inert gas used in this free sulfur removal process is not particularly limited, and nitrogen gas, argon gas, and the like may be used.

The flow rate of the inert gas at the time of performing this free sulfur removal process is not particularly limited, and is preferably 50 to 200 mL/min, and more preferably 100 to 150 mL/min, relative to 10 g of the crude product, from the viewpoint of removing the sulfur vapor generated upon heating, from the reaction product.

The reaction temperature and the retention time in the free sulfur removal process are not particularly limited.

Although it also depends on the amount of the sulfur residue, the reaction temperature is usually a temperature at which sulfur vaporizes and/or sublimates, i.e., 250 to 350° C., and preferably 270 to 330° C. The retention time is usually 0.5 to 5 hours, and preferably 1 to 3 hours.

3. Battery

The organic sulfur material of the present invention has excellent characteristics as described above. Specifically, the sulfur is trapped within the carbide, and a majority of the carbide forms an undeveloped graphene skeleton, by which a carbon skeleton with relatively high conductivity and structure flexibility is formed; thus, the organic sulfur material of the present invention has a structure that can withstand the expansion and shrinkage caused by charge and discharge. Taking advantage of such structural characteristics, the organic sulfur material of the present invention is effectively used as an electrode active material (in particular, a cathode active material) of lithium batteries (in particular, lithium-ion secondary batteries), such as lithium primary batteries, lithium-ion secondary batteries (e.g., lithium-ion secondary batteries and metal lithium secondary batteries); an electrode active material (in particular, a cathode active material) of sodium-ion secondary batteries; an electrode active material (in particular, a cathode active material) of magnesium-ion secondary batteries; and the like. In particular, the organic sulfur material of the present invention is a high-capacity material having a high conductivity, possibly achieves improved cycle characteristics, and is thus useful as an electrode active material (in particular, a cathode active material) of secondary batteries, such as lithium-ion secondary batteries.

A secondary battery, such as a lithium-ion secondary battery, comprising the organic sulfur material of the present invention as an electrode active material (in particular, a cathode active material) for a secondary battery, such as a lithium-ion secondary battery, may be used as either a non-aqueous electrolyte lithium-ion secondary battery containing, as an electrolyte, a non-aqueous solvent-based electrolyte solution, or an all-solid-state lithium-ion secondary battery containing, as an electrolyte, a lithium-ion conductive solid electrolyte.

The non-aqueous electrolyte lithium-ion secondary battery and all-solid-state lithium-ion secondary battery may have the same structure as that of a known lithium-ion secondary battery, except for the use of the organic sulfur material of the present invention as an electrode active material (in particular, a cathode active material).

For example, the non-aqueous electrolyte lithium-ion secondary battery may have the same basic structure as that of a known non-aqueous electrolyte lithium-ion secondary battery, except for the use of the organic sulfur material of the present invention described above, as an electrode active material (in particular, a cathode active material).

Regarding the cathode, the organic sulfur material of the present invention may be used as a cathode active material. For example, a positive electrode prepared by mixing the organic sulfur material of the present invention with a conductive material and a binder may be supported by a cathode collector, such as Al, Ni, stainless, or carbon cloth. Examples of usable conductive materials include carbon materials, such as graphite, cokes, carbon black, and acicular carbon. When the organic sulfur material of the present invention is used as an anode active material, previously known materials may be used as a cathode, and existing materials such as lithium cobalt oxide ($LiCoO_2$), lithium nickel oxide ($LiNiO_2$), lithium manganese oxide ($LiMn_2O_4$), lithium iron phosphate ($LiFePO_4$), vanadium oxide materials, and sulfur materials may be used as a cathode active material.

An anode for use may be either a lithium-containing material or a lithium-free material. Examples include metal lithium, tin, silicon, alloys containing these metals, SiO, and the like, as well as graphite and sintering-resistant carbon. When a lithium-free material is used, a material in which lithium is pre-doped may be used. These anode active materials may also optionally be supported by an anode collector, such as Al, Cu, Ni, stainless, or carbon, using the conductive materials described above, binders, etc. The organic sulfur material of the present invention may also be used as an anode active material.

Examples of separators for use include materials in the form of porous film, non-woven fabric, and woven fabric that are made of polyolefin resin, such as polyethylene and polypropylene, fluororesin, nylon, aromatic aramid, and inorganic glass.

The solvent usable for non-aqueous electrolytes include known solvents for non-aqueous solvent-based secondary batteries, such as carbonates, ethers, nitriles, and sulfur-containing compounds.

The all-solid-state lithium-ion secondary battery may also have the same structure as that of a known all-solid-state lithium-ion secondary battery, except for the use of the organic sulfur material of the present invention as an electrode active material (in particular, a cathode active material).

In this case, examples of usable lithium-ion conductive solid electrolytes include polymer-based solid electrolytes such as polyethylene oxide-based polymers and polymers containing at least one of a polyorganosiloxane chain and a polyoxyalkylene chain; sulfide-based solid electrolytes; and oxide-based solid electrolytes.

Regarding the cathode of all-solid-state lithium-ion secondary batteries, the organic sulfur material of the present invention may be used as a cathode active material. For example, a positive electrode containing the organic sulfur material of the present invention, a conductive material, a binder, and a solid electrolyte may be supported by a cathode collector, such as Ti, Al, Ni, or stainless. Examples of usable conductive materials include carbon materials, such as graphite, cokes, carbon black, and acicular carbon, as with the non-aqueous electrolyte lithium-ion secondary batteries. When the organic sulfur material of the present invention is used as an anode active material, existing materials such as lithium cobalt oxide ($LiCoO_2$), lithium nickel oxide ($LiNiO_2$), lithium manganese oxide ($LiMn_2O_4$), lithium iron phosphate ($LiFePO_4$), vanadium oxide materials, and sulfur materials may be used as a cathode active material.

An anode for use may be either a lithium-containing material or a lithium-free material, as with the non-aqueous electrolyte lithium-ion secondary batteries. Examples include metal lithium, tin, silicon, alloys containing these metals, SiO, and the like, as well as graphite and sintering-resistant carbon. When a lithium-free material is used, a material in which lithium is pre-doped may be used. These anode active materials may also optionally be supported by an anode collector, such as Al, Cu, Ni, stainless, or carbon, using the conductive materials described above, binders, etc. The organic sulfur material of the present invention may also be used as an anode active material.

There is also no particular limitation on the shape of non-aqueous electrolyte lithium-ion secondary batteries and all-solid-state lithium-ion secondary batteries. These batteries may have any shape, such as a cylindrical shape or prismatic shape.

EXAMPLES

The present invention is described below in more detail with reference to Examples. However, the present invention is, needless to say, not limited to these Examples.

Example 1

1-Octanol (Non-Aqueous Electrolyte Lithium Secondary Battery)

Sulfur (Kishida Chemical Co., Ltd., purity: 99%) (5.065 g) and 1.6474 g of 1-octanol (Wako Pure Chemical Industries, Ltd., purity 98%) (the buoyancy correction was not made for weighing to the nearest 0.1 mg; the same applies hereinafter) were placed in a test tube (produced by Maruemu Corporation, A-30, 30 mm (diameter)×200 mm (length)), and a silicone rubber stopper provided with an alumina protective tube (SSA-S, inner diameter: 2 mm, outer diameter: 4 mm, length: 230 mm) was attached. This rubber stopper is provided with holes for introducing or discharging nitrogen gas, and a hole for inserting a thermocouple (FIG. 1). The lower part of the test tube, 100 mm from the bottom, was placed in the heating portion of an electric furnace, and heating was initiated while introducing nitrogen gas at a rate of 50 mL per minute. The upper part of the test tube was exposed to open air to be cooled. The thermocouple was positioned inside the reaction solution at the lower part of the test tube, and the sample temperature (reaction solution temperature) was directly measured. About 1 hour later, the sample temperature reached 398° C. At this time, the solution went up as a vapor to the upper part of the test tube, cooled off at the upper part, and adhered as droplets to the wall of the test tube; thus, 1-octanol, which is a carbon source, was confirmed to be refluxing as a liquid. Then, after heating was stopped, the temperature was maintained at 300° C. or higher for 30 minutes (at 380° C. or higher for 5 minutes). After being allowed to cool naturally to room temperature, the reaction product inside the test tube was removed and placed in a quartz boat, which was set at the center of a quartz tube (inner diameter: 30 mm, length: 900 mm), and maintained at 300° C. for 2 hours under a nitrogen stream to thus vaporize and remove the sulfur. After cooling, 0.1634 g of black solid powder (organic sulfur material) was obtained.

Figure 2:
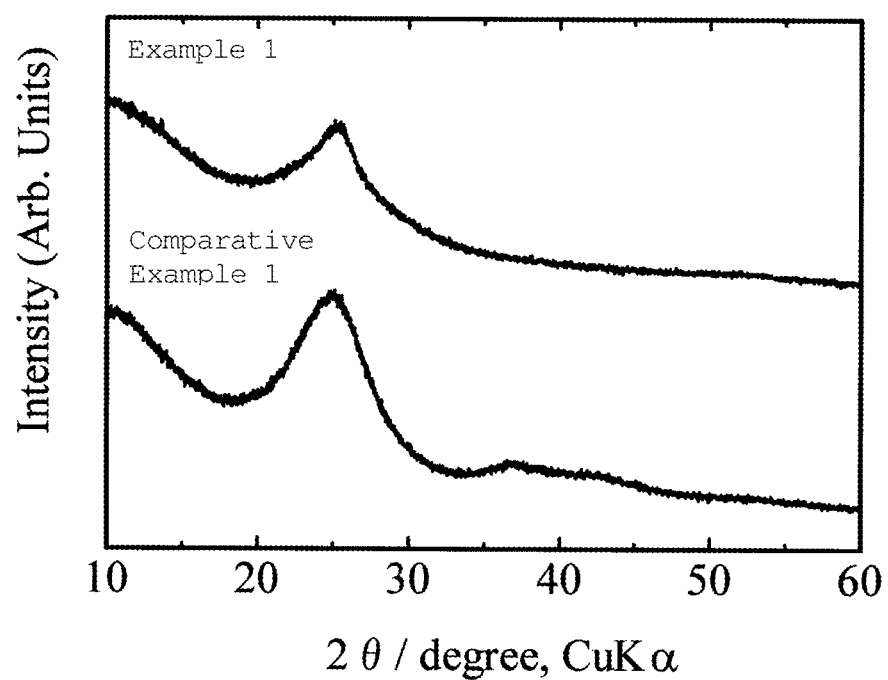
FIG. 2 is a graph showing X-ray diffraction patterns of the organic sulfur materials obtained in Example 1 and Comparative Example 1 (10-60°).

As shown in FIG. 2, the X-ray diffraction pattern of the obtained sample only showed a wide peak at about 2θ=25°, which indicates that the sample was an amorphous material. Further, there were no peaks originating from elemental sulfur; thus, the existence of sulfur residue (free sulfur) was not confirmed.

Figure 3:
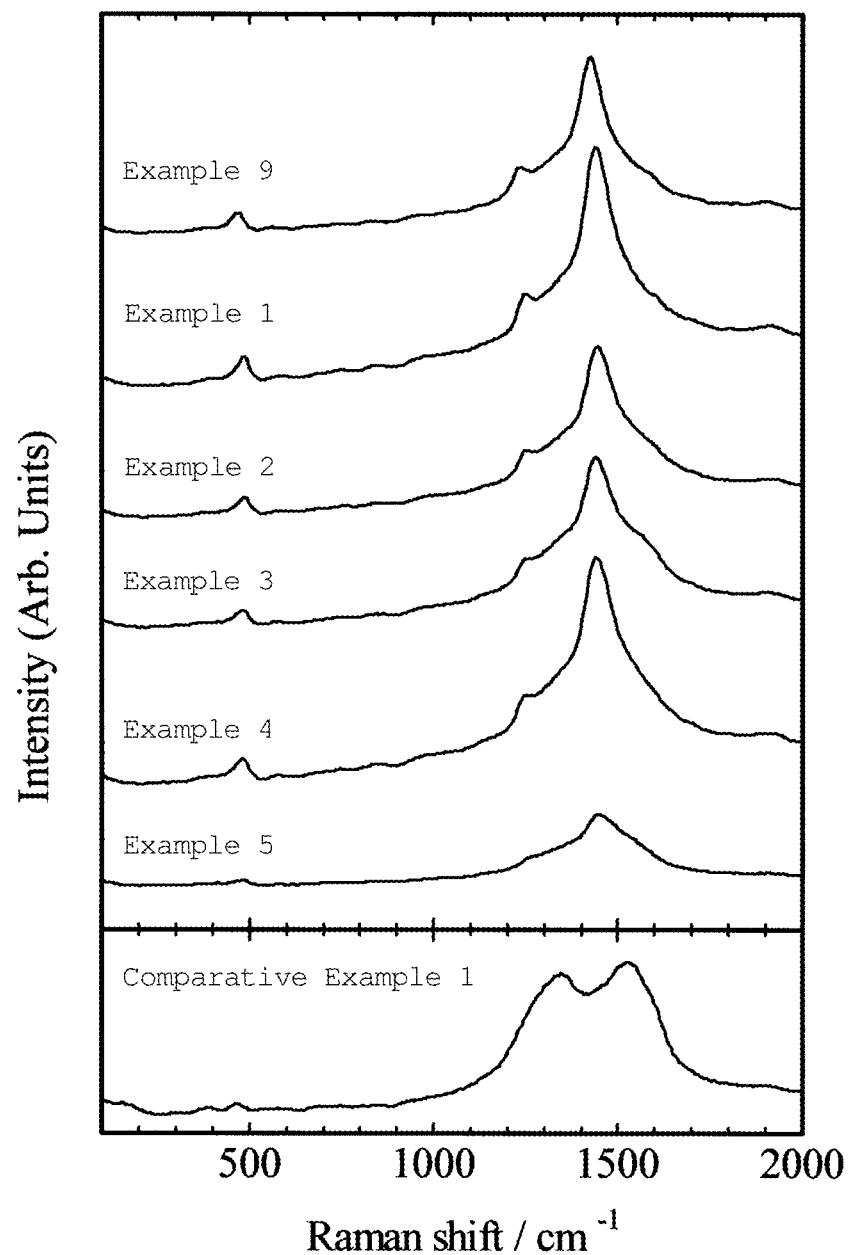
FIG. 3 is a graph showing Raman spectra (100-2000 cm$^{-1}$) of the organic sulfur materials obtained in Examples 1 to 5 and 9, and Comparative Example 1.
Figure 4:
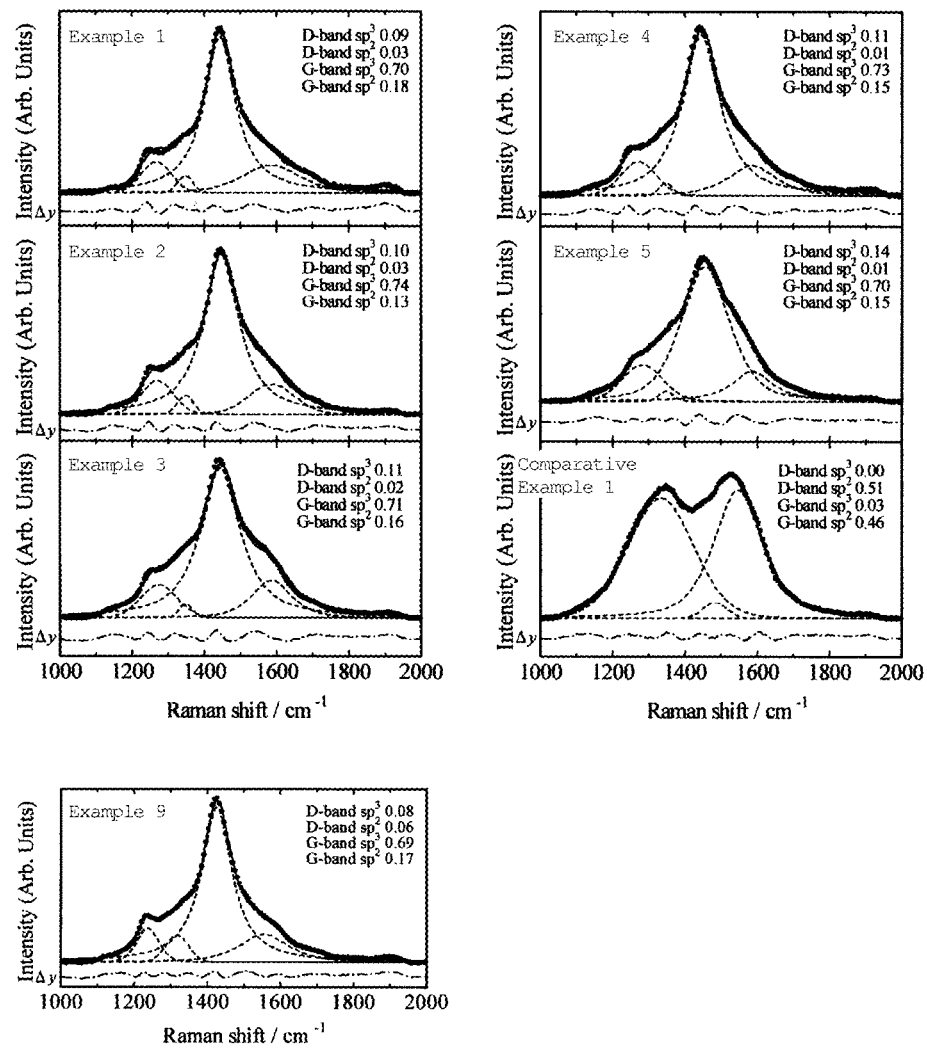
FIG. 4 is graphs showing the deconvolution of the Raman spectrum (1000-2000 cm$^{-1}$) into four components for each organic sulfur material obtained in Examples 1 to 5 and 9, and Comparative Example 1.

As shown in FIG. 3, the Raman spectrum of the obtained sample showed a main peak at 1440 cm$^{-1}$, as well as peaks at 1900 cm$^{-1}$, 1250 cm$^{-1}$, and 480 cm$^{-1}$. The following are the relations of peak intensities: the peak intensity at 1900 cm$^{-1}$ was about 0.07 times the peak intensity at 1440 cm$^{-1}$, the peak intensity at 1250 cm$^{-1}$ was about 0.31 times the peak intensity at 1440 cm$^{-1}$, and the peak intensity at 480 cm$^{-1}$ was about 0.09 times the peak intensity at 1440 cm$^{-1}$. No peaks were observed in the vicinity of 1066 cm$^{-1}$ or 846 cm$^{-1}$. Further, fitting was performed with respect to 4 components (the sp$^3$ component of the D band (1270 cm$^{-1}$), the sp$^2$ component of the D band (1350 cm$^{-1}$), the sp$^3$ component of the G band (1440 cm$^{-1}$), and the sp$^2$ component of the G band (1590 cm$^{-1}$)) of the spectrum from 1000 to 2000 cm$^{-1}$, which relates to carbon components. As a result, as shown in FIG. 4, the population of the sp$^3$ component of the G band was 70%.

Figure 5:
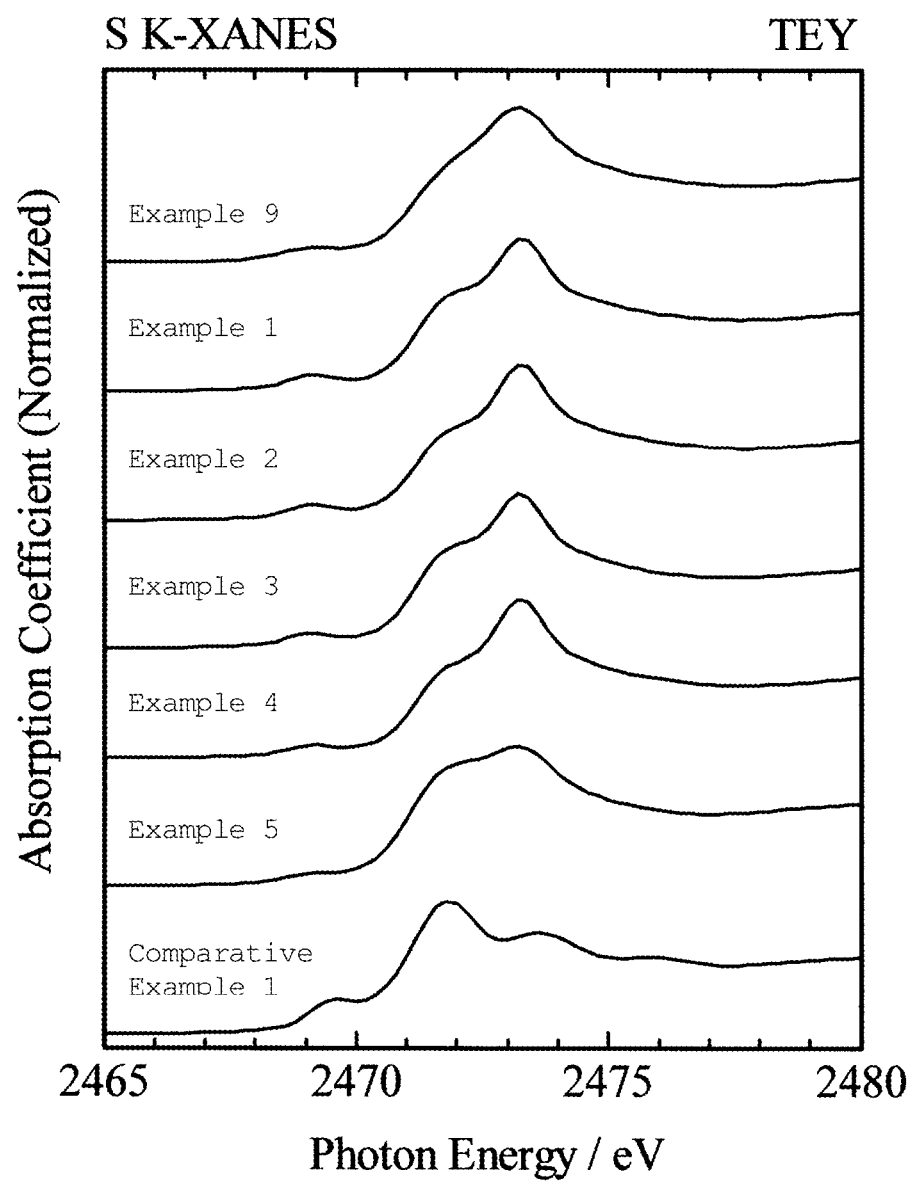
FIG. 5 is a graph showing X-ray absorption fine structure (XAFS) spectra of the organic sulfur materials obtained in Examples 1 to 5 and 9, and Comparative Example 1 (2465-2480 eV).

Further, as shown in FIG. 5, the XAFS spectrum showed a main absorption peak at 2473 eV, as well as absorption peaks at 2469 eV and 2472 eV. The following are the relations of peak intensities: the peak intensity at 2469 eV was about 0.11 times the peak intensity at 2473 eV, and the peak intensity at 2472 eV was about 0.66 times the peak intensity at 2473 eV.

According to elemental analysis using the combustion method, the carbon content was 34.4 wt %, the sulfur content was 65.7 wt %, the hydrogen content was 0.4 wt %, and the oxygen and nitrogen were below the detection limit (less than 0.01 wt %).

Accordingly, an organic sulfur material was obtained, which contained carbonized components, e.g., a graphene skeleton, and contained a carbon-sulfur bond.

Figure 6:
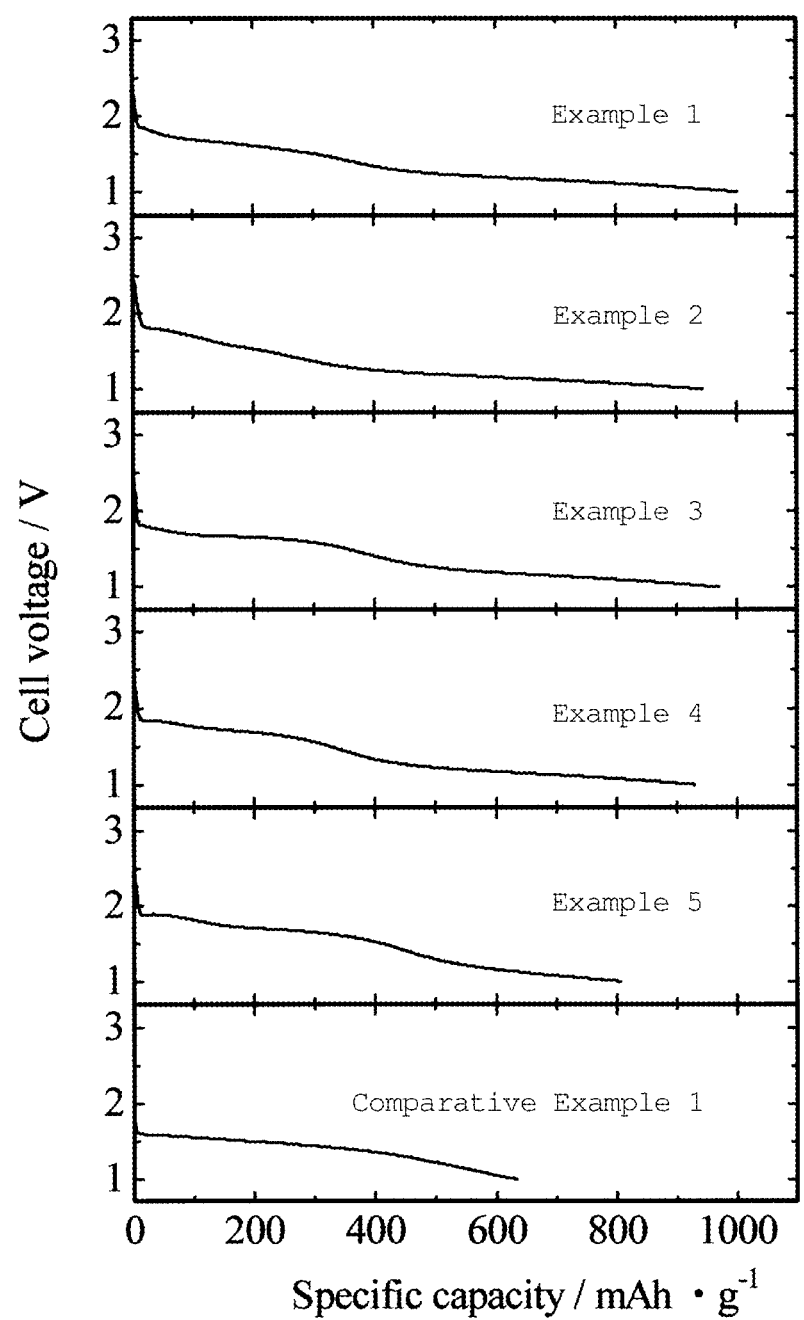
FIG. 6 is a graph showing the charge-and-discharge test results of the non-aqueous electrolyte lithium secondary batteries obtained in Examples 1 to 5, and Comparative Example 1.

A charge and discharge test was then conducted by using galvanostatic measurement at a current density of 30 mA/g and at a cutoff voltage of 1.0 to 3.0 V by starting from discharge, using the obtained organic sulfur material as a cathode active material, a lithium metal as an anode, an aluminum mesh as a collector, and an electrolyte solution obtained by dissolving LiPF$_6$ in an ethylene carbonate-dimethyl carbonate mixture liquid. FIG. 6 shows the charge and discharge characteristics. The initial discharge capacity was 1000 mAh/g, which was higher than that of the organic sulfur material (mentioned below) obtained using polyacrylonitrile (PAN) as a starting material (Comparative Example 1; 630 mAh/g).

The results indicate that the production of an organic sulfur material under the conditions adopted in the present invention and use of the material as a cathode active material of a non-aqueous electrolyte lithium secondary battery led the lithium secondary battery to have a high capacity.

Example 2

1-Heptanol (Non-Aqueous Electrolyte Lithium Secondary Battery)

An organic sulfur material was produced as in Example 1, except that 1-heptanol was used as a linear or branched alcohol. Specifically, 4.1107 g of sulfur and 1.2121 g of 1-heptanol (Kishida Chemical Co., Ltd., purity: 98%) were placed in a test tube and heated to a sample temperature of 459° C. in an electric furnace under nitrogen gas stream (50 mL/min). At this time, the solution went up as a vapor to the upper part of the test tube, cooled off at the upper part, and adhered as droplets to the wall of the test tube; thus, 1-heptanol, which is a carbon source, was confirmed to be refluxing as a liquid. Then, after heating was stopped, the temperature was maintained at 300° C. or higher for 30 minutes (at 380° C. or higher for 10 minutes). The temperature was lowered to room temperature, and the obtained reaction product was heated under nitrogen stream at 300° C. for 2 hours to vaporize and remove the sulfur to thus obtain 0.2803 g of black powder (organic sulfur material).

The X-ray diffraction pattern of the obtained sample only showed, as in Example 1, a wide peak at about 2θ=25°, which indicates that the sample was an amorphous material.

Further, there were no peaks originating from elemental sulfur; thus, the existence of sulfur residue (free sulfur) was not confirmed.

As shown in FIG. 3, the Raman spectrum of the obtained sample showed a main peak at 1440 cm$^{-1}$, as well as peaks at 1900 cm$^{-1}$, 1250 cm$^{-1}$, and 480 cm$^{-1}$. The following are the relations of peak intensities: the peak intensity at 1900 cm$^{-1}$ was about 0.08 times the peak intensity at 1440 cm$^{-1}$, the peak intensity at 1250 cm$^{-1}$ was about 0.33 times the peak intensity at 1440 cm$^{-1}$, and the peak intensity at 480 cm$^{-1}$ was about 0.08 tims the peak intensity at 1440 cm$^{-1}$. No peaks were observed in the vicinity of 1066 cm$^{-1}$ or 846 cm$^{-1}$. Further, fitting was performed with respect to 4 components (the sp$^3$ component of the D band (1270 cm$^{-1}$), the sp$^2$ component of the D band (1350 cm$^{-1}$), the sp$^3$ component of the G band (1440 cm), and the sp$^2$ component of the G band (1590 cm$^{-1}$)) of the spectrum from 1000 to 2000 cm$^{-1}$, which relates to carbon components. As a result, as shown in FIG. 4, the population of the sp$^3$ component of the G band was 74%.

Further, as shown in FIG. 5, the XAFS spectrum showed a main absorption peak at 2473 eV, as well as absorption peaks at 2469 eV and 2472 eV. The following are the relations of peak intensities: the peak intensity at 2469 eV was about 0.10 times the peak intensity at 2473 eV, and the peak intensity at 2472 eV was about 0.61 times the peak intensity at 2473 eV.

According to elemental analysis using the combustion method, the carbon content was 36.2 wt %, the sulfur content was 63.3 wt %, the hydrogen content was 0.3 wt %, and the oxygen and nitrogen were below the detection limit (less than 0.01 wt %).

Accordingly, an organic sulfur material was obtained, which contained carbonized components, e.g., a graphene skeleton, and contained a carbon-sulfur bond.

The charge and discharge test was conducted in completely the same manner as in Example 1, except that this organic sulfur material was used as a cathode active material of a non-aqueous electrolyte lithium secondary battery. FIG. 6 shows the charge and discharge characteristics. The initial discharge capacity was 940 mAh/g, which was higher than that of the organic sulfur material, described below, obtained using polyacrylonitrile (PAN) as a starting material (Comparative Example 1; 630 mAh/g).

The results indicate that the production of an organic sulfur material under the conditions adopted in the present invention and use of the material as a cathode active material of a non-aqueous electrolyte lithium secondary battery led the lithium secondary battery to have a high capacity.

Example 3

1-Hexanol (Non-Aqueous Electrolyte Lithium Secondary Battery)

An organic sulfur material was produced as in Example 1, except that 1-hexanol was used as a linear or branched alcohol. Specifically, 3.6000 g of sulfur and 1.2119 g of 1-hexanol (Kishida Chemical Co., Ltd., purity: 99%) were placed in a test tube and heated to a sample temperature of 450° C. in an electric furnace under nitrogen gas stream (50 mL/min). At this time, the solution went up as a vapor to the upper part of the test tube, cooled off at the upper part, and adhered as droplets to the wall of the test tube; thus 1-hexanol, which is a carbon source, was confirmed to be refluxing as a liquid. Then, after heating was stopped, the temperature was maintained at 300° C. or higher for 30 minutes (at 380° C. or higher for 10 minutes). The temperature was lowered to room temperature, and the obtained reaction product was heated under nitrogen stream at 300° C. for 2 hours to vaporize and remove the sulfur to thus obtain 0.3135 g of black powder (organic sulfur material).

The X-ray diffraction pattern of the obtained sample only showed, as in Example 1, a wide peak at about 2θ=25°, which indicates that the sample was an amorphous material. Further, there were no peaks originating from elemental sulfur; thus, the existence of sulfur residue (free sulfur) was not confirmed.

As shown in FIG. 3, the Raman spectrum of the obtained sample showed a main peak at 1440 cm$^{-1}$, as well as peaks at 1900 cm$^{-1}$, 1250 cm$^{-1}$, and 480 cm$^{-1}$. The following are the relations of peak intensities: the peak intensity at 1900 cm$^{-1}$ was about 0.09 times the peak intensity at 1440 cm$^{-1}$, the peak intensity at 1250 cm$^{-1}$ was about 0.35 times the peak intensity at 1440 cm$^{-1}$, and the peak intensity at 480 cm$^{-1}$ was about 0.08 times the peak intensity at 1440 cm$^{-1}$. No peaks were observed in the vicinity of 1066 cm$^{-1}$ or 846 cm$^{-1}$. Further, fitting was performed with respect to 4 components (the sp$^3$ component of the D band (1270 cm$^{-1}$), the sp$^2$ component of the D band (1350 cm$^{-1}$), the sp$^3$ component of the G band (1440 cm$^{-1}$), and the sp$^2$ component of the G band (1590 cm$^{-1}$)) of the spectrum from 1000 to 2000 cm$^{-1}$, which relates to carbon components. As a result, as shown in FIG. 4, the population of the sp$^3$ component of the G band was 71%.

Further, as shown in FIG. 5, the XAFS spectrum showed a main absorption peak at 2473 eV, as well as absorption peaks at 2469 eV and 2472 eV. The following are the relations of peak intensities: the peak intensity at 2469 eV was about 0.10 times the peak intensity at 2473 eV, and the peak intensity at 2472 eV was about 0.68 times the peak intensity at 2473 eV.

According to elemental analysis using the combustion method, the carbon content was 33.8 wt %, the sulfur content was 66.1 wt %, the hydrogen content was 0.2 wt %, and the oxygen and nitrogen were below the detection limit (less than 0.01 wt %).

Accordingly, an organic sulfur material was obtained, which contained carbonized components, e.g., a graphene skeleton, and contained a carbon-sulfur bond.

The charge and discharge test was conducted in completely the same manner as in Example 1, except that this organic sulfur material was used as a cathode active material of a non-aqueous electrolyte lithium secondary battery. FIG. 6 shows the charge and discharge characteristics. The initial discharge capacity was 970 mAh/g, which was higher than that of the organic sulfur material, described below, obtained using polyacrylonitrile (PAN) as a starting material (Comparative Example 1; 630 mAh/g).

The results indicate that the production of an organic sulfur material under the conditions adopted in the present invention and use of the material as a cathode active material of a non-aqueous electrolyte lithium secondary battery led the lithium secondary battery to have a high capacity.

Example 4

1-Pentanol (Non-Aqueous Electrolyte Lithium Secondary Battery)

An organic sulfur material was produced as in Example 1, except that 1-pentanol was used as a linear or branched alcohol. Specifically, 3.9416 g of sulfur and 1 mL (0.811 g) of 1-pentanol (Kishida Chemical Co., Ltd., purity: 98%)

were placed in a test tube, and heated to a sample temperature of 445° C. in an electric furnace under nitrogen gas stream (50 mL/min). At this time, the solution went up as a vapor to the upper part of the test tube, cooled off at the upper part, and adhered as droplets to the wall of the test tube; thus, 1-pentanol, which is a carbon source, was confirmed to be refluxing as a liquid. Then, after heating was stopped, the temperature was maintained at 300° C. or higher for 30 minutes (at 380° C. or higher for 10 minutes). The temperature was lowered to room temperature, and the obtained reaction product was heated under nitrogen stream at 300° C. for 2 hours to vaporize and remove the sulfur to thus obtain 0.1688 g of black powder (organic sulfur material).

The X-ray diffraction pattern of the obtained sample only showed, as in Example 1, a wide peak at about 2θ=25°, which indicates that the sample was an amorphous material. Further, there were no peaks originating from elemental sulfur; thus, the existence of sulfur residue (free sulfur) was not confirmed.

As shown in FIG. 3, the Raman spectrum of the obtained sample showed a main peak at 1440 cm$^{-1}$, as well as peaks at 1900 cm$^{-1}$, 1250 cm$^{-1}$, and 480 cm$^{-1}$. The following are the relations of peak intensities: the peak intensity at 1900 cm$^{-1}$ was about 0.06 times the peak intensity at 1440 cm$^{-1}$, the peak intensity at 1250 cm$^{-1}$ was about 0.32 times the peak intensity at 1440 cm$^{-1}$, and the peak intensity at 480 cm$^{-1}$ was about 0.08 times the peak intensity at 1440 cm$^{-1}$. No peaks were observed in the vicinity of 1066 cm$^{-1}$ or 846 cm$^{-1}$. Further, fitting was performed with respect to 4 components (the sp$^3$ component of the D band (1270 cm$^{-1}$), the sp$^2$ component of the D band (1350 cm$^{-1}$), the sp$^3$ component of the G band (1440 cm$^{-1}$), and the sp$^2$ component of the G band (1590 cm$^{-1}$)) of the spectrum from 1000 to 2000 cm$^{-1}$, which relates to carbon components. As a result, as shown in FIG. 4, the population of the sp$^3$ component of the G band was 73%.

Further, as shown in FIG. 5, the XAFS spectrum showed a main absorption peak at 2473 eV, as well as absorption peaks at 2469 eV and 2472 eV. The following are the relations of peak intensities: the peak intensity at 2469 eV was about 0.09 times the peak intensity at 2473 eV, and the peak intensity at 2472 eV was about 0.61 times the peak intensity at 2473 eV.

According to elemental analysis using the combustion method, the carbon content was 34.9 wt %, the sulfur content was 62.6 wt %, the hydrogen content was 0.2 wt %, and the oxygen and nitrogen were below the detection limit (less than 0.01 wt %).

Accordingly, an organic sulfur material was obtained, which contained carbonized components, e.g., a graphene skeleton, and contained a carbon-sulfur bond.

The charge and discharge test was conducted in completely the same manner as in Example 1, except that this organic sulfur material was used as a cathode active material of a non-aqueous electrolyte lithium secondary battery. FIG. 6 shows the charge and discharge characteristics. The initial discharge capacity was 930 mAh/g, which was higher than that of the organic sulfur material, described below, obtained using polyacrylonitrile (PAN) as a starting material (Comparative Example 1; 630 mAh/g).

The results indicate that the production of an organic sulfur material under the conditions adopted in the present invention and use of the material as a cathode active material of a non-aqueous electrolyte lithium secondary battery led the lithium secondary battery to have a high capacity.

Example 5

1-Butanol (Non-Aqueous Electrolyte Lithium Secondary Battery)

An organic sulfur material was produced as in Example 1, except that 1-butanol was used as a linear or branched alcohol. Specifically, 3.5673 g of sulfur, 1.2356 g of 1-butanol (Kishida Chemical Co., Ltd., purity: 99.5%), and 0.7201 g of hydrazine monohydrate (Kishida Chemical Co., Ltd., purity: 98%) were placed in a test tube, and heated to a sample temperature of 411° C. in an electric furnace under nitrogen gas stream (50 mL/min). At this time, the solution went up as a vapor to the upper part of the test tube, cooled off at the upper part, and adhered as droplets to the wall of the test tube; thus, 1-butanol, which is a carbon source, and hydrazine were confirmed to be refluxing as a liquid. Then, after heating was stopped, the temperature was maintained at 300° C. or higher for 30 minutes (at 380° C. or higher for 7 minutes). The temperature was lowered to room temperature, and the obtained reaction product was heated under nitrogen stream at 300° C. for 2 hours to vaporize and remove the sulfur to thus obtain 0.0918 g of black solid powder (organic sulfur material).

The X-ray diffraction pattern of the obtained sample only showed, as in Example 1, a wide peak at about 2θ=25°, which indicates that the sample was an amorphous material. Further, there were no peaks originating from elemental sulfur; thus, the existence of sulfur residue (free sulfur) was not confirmed.

As shown in FIG. 3, the Raman spectrum of the obtained sample showed a main peak at 1440 cm$^{-1}$, as well as peaks at 1900 cm$^{-1}$, 1250 cm$^{-1}$, and 480 cm$^{-1}$. The following are the relations of peak intensities: the peak intensity at 1900 cm$^{-1}$ was about 0.07 times the peak intensity at 1440 cm$^{-1}$, the peak intensity at 1250 cm$^{-1}$ was about 0.30 times the peak intensity at 1440 cm$^{-1}$, and the peak intensity at 480 cm$^{-1}$ was about 0.06 times the peak intensity at 1440 cm$^{-1}$. No peaks were observed in the vicinity of 1066 cm$^{-1}$ or 846 cm$^{-1}$. Further, fitting was performed with respect to 4 components (the sp$^3$ component of the D band (1270 cm$^{-1}$), the sp$^2$ component of the D band (1350 cm$^{-1}$), the sp$^3$ component of the G band (1440 cm$^{-1}$), and the sp$^2$ component of the G band (1590 cm$^{-1}$)) of the spectrum from 1000 to 2000 cm$^{-1}$, which relates to carbon components. As a result, as shown in FIG. 4, the population of the sp$^3$ component of the G band was 70%.

Further, as shown in FIG. 5, the XAFS spectrum showed a main absorption peak at 2473 eV, as well as absorption peaks at 2469 eV and 2472 eV. The following are the relations of peak intensities: the peak intensity at 2469 eV was about 0.09 times the peak intensity at 2473 eV, and the peak intensity at 2472 eV was about 0.88 times the peak intensity at 2473 eV.

According to elemental analysis using the combustion method, the carbon content was 36.3 wt %, the sulfur content was 60.6 wt %, the hydrogen content was 0.3 wt %, and the oxygen and nitrogen were below the detection limit (less than 0.01 wt %).

Accordingly, an organic sulfur material was obtained, which contained carbonized components, e.g., a graphene skeleton, and contained a carbon-sulfur bond.

The charge and discharge test was conducted in completely the same manner as in Example 1, except that this organic sulfur material was used as a cathode active material of a non-aqueous electrolyte lithium secondary battery. FIG. 6 shows the charge and discharge characteristics. The initial discharge capacity was 810 mAh/g, which was higher than that of the organic sulfur material, described below, obtained using polyacrylonitrile (PAN) as a starting material (Comparative Example 1; 630 mAh/g).

The results indicate that the production of an organic sulfur material under the conditions adopted in the present invention and use of the material as a cathode active material of a non-aqueous electrolyte lithium secondary battery led the lithium secondary battery to have a high capacity.

Comparative Example 1

Polyacrylonitrile (Non-Aqueous Electrolyte Lithium Secondary Battery)

An organic sulfur material (PAN-S) was produced by using completely the same method disclosed in NPL 3. Specifically, 3.9972 g of polyacrylonitrile (PAN; Aldrich, average molecular weight: 150000, purity: 95%) and 4.8182 g of sulfur (Kishida Chemical Co., Ltd., purity: 99%) were mixed at a weight ratio of 1:1.2, placed in a glass vessel, and heated in a quartz tube to 300° C. in a nitrogen gas atmosphere. Then, heating was stopped, the temperature was lowered to room temperature, and 5.5091 g of black solid powder (PAN-S) was obtained.

As shown in FIG. 2, the X-ray diffraction pattern of the obtained sample only showed a wide peak at about $2\theta=25°$, which indicates that the sample was an amorphous material. This conforms well to the results reported in PTL 1, NPL 3, etc.

As shown in FIG. 3, the Raman spectrum of the obtained sample showed main peaks in the vicinity of 1350 $cm^{-1}$ and 1530 $cm^{-1}$. This conforms well to the results of PTL 1, and the spectrum obtained here was different from those of Examples 1 to 5. Further, fitting was performed with respect to 4 components (the $sp^3$ component of the D band (1270 $cm^{-1}$), the $sp^2$ component of the D band (1350 $cm^{-1}$), the $sp^3$ component of the G band (1440 $cm^{-1}$), and the $sp^2$ component of the G band (1590 $cm^{-1}$)) of the spectrum from 1000 to 2000 $cm^{-1}$, which relates to carbon components. As a result, as shown in FIG. 4, the population of the $sp^3$ component of the G band was 3%, which is completely different from that of Examples 1 to 5.

Furthermore, as shown in FIG. 5, the XAFS spectrum showed a main peak in the vicinity of 2471.7 eV, as well as absorption peaks in the vicinity of 2469.5 eV and the 2473.5 eV, which were completely different from those of Examples 1 to 5.

The above results confirm that the target organic sulfur material cannot be produced when a linear or branched alcohol, a linear or branched carboxylic acid, a linear or branched aldehyde, or the like is not used as a starting material.

The charge and discharge test was conducted as in Example 1, except that the obtained organic sulfur material (PAN-S) was used as a cathode active material. FIG. 6 shows the charge and discharge characteristics. The initial discharge capacity was 630 mAh/g, which conforms well with the results disclosed in NPL 3, and is lower than that of Examples of 1 to 5.

Example 6

1-Octanol (All-Solid-State Lithium-ion Secondary Battery)

An all-solid-state lithium-ion secondary battery was assembled using the organic sulfur material obtained in Example 1 as a cathode active material, a lithium-indium alloy as an anode, and $75Li_2S$-$25P_2S_5$ as an electrolyte. Subsequently, a charge and discharge test was conducted. The organic sulfur material described above, the $75Li_2S$-$25P_2S_5$ electrolyte, and a carbon powder were mixed at a weight ratio of 4:6:0.6, and used as a positive electrode. The positive electrode, the $75Li_2S$-$25P_2S_5$ electrolyte, and the lithium-indium alloy were laminated in this order, and molded by applying pressure, thereby producing a pellet battery with a diameter of 10 mm. A charge and discharge test was then conducted using this battery by galvanostatic measurement at a current density of 30 mA/g (150 $\mu A/cm^2$) and at a cutoff voltage of 0.4 to 3.0 V by starting from discharge.

Figure 7:
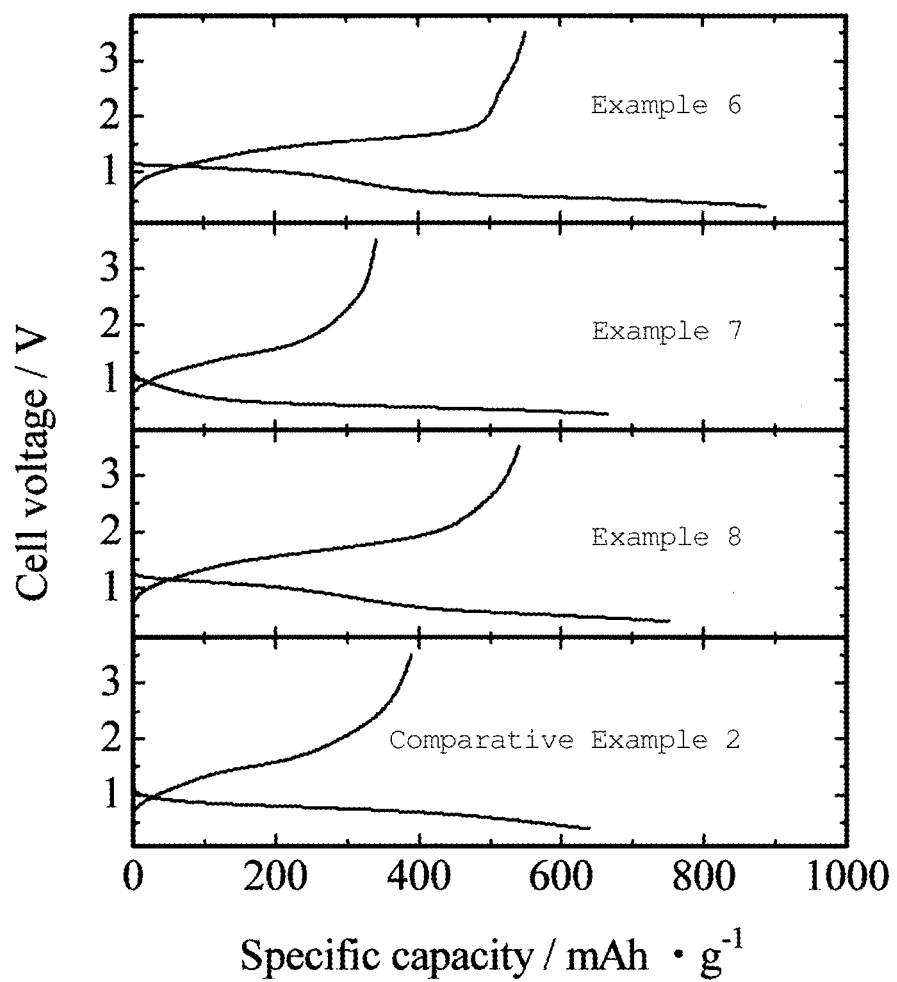
FIG. 7 is a graph showing the charge-and-discharge test results of the all-solid-state lithium-ion secondary batteries obtained in Examples 6 to 8, and Comparative Example 2.

FIG. 7 shows the charge and discharge characteristics. The initial discharge capacity was 890 mAh/g, which was higher than that of the organic sulfur material, described below, obtained using polyacrylonitrile (PAN) as a starting material (Comparative Example 2; 640 mAh/g). Further, the discharge capacity after 10 cycles was about 270 mAh/g (capacity retention: 30%), demonstrating a relatively excellent reversible cycle.

The results indicate that the production of an organic sulfur material under the conditions adopted in the present invention and use of the material as a cathode active material of an all-solid-state lithium-ion secondary battery led the all-solid-state lithium-ion secondary battery to have a high capacity and excellent reversible cycle characteristics.

Example 7

1-Heptanol (All-Solid-State Lithium-ion Secondary Battery)

The charge and discharge test was conducted as in Example 6, except that the organic sulfur material obtained in Example 2 was used as a cathode active material. FIG. 7 shows the charge and discharge characteristics. The initial discharge capacity was 660 mAh/g, which was higher than that of the organic sulfur material, described below, obtained using polyacrylonitrile (PAN) as a starting material (Comparative Example 2; 640 mAh/g). Further, the discharge capacity after 10 cycles was about 160 mAh/g (capacity retention: 24%), demonstrating a relatively excellent reversible cycle.

The results indicate that the production of an organic sulfur material under the conditions adopted in the present invention and use of the material as a cathode active material of an all-solid-state lithium-ion secondary battery led the all-solid-state lithium-ion secondary battery to have a high capacity and excellent reversible cycle characteristics.

Example 8

1-Hexanol (All-Solid-State Lithium-ion Secondary Battery)

The charge and discharge test was conducted as in Example 6, except that the organic sulfur material obtained in Example 3 was used as a cathode active material. FIG. 7 shows the charge and discharge characteristics. The initial discharge capacity was 750 mAh/g, which was higher than that of the organic sulfur material, described below, obtained using polyacrylonitrile (PAN) as a starting material (Comparative Example 2; 640 mAh/g). Further, the discharge capacity after 10 cycles was about 240 mAh/g (capacity retention: 31%), demonstrating a relatively excellent reversible cycle.

The results indicate that the production of an organic sulfur material under the conditions adopted in the present invention and use of the material as a cathode active material of an all-solid-state lithium-ion secondary battery led the all-solid-state lithium-ion secondary battery to have a high capacity and excellent reversible cycle characteristics.

Comparative Example 2

Polyacrylonitrile (All-Solid-State Lithium-ion Secondary Battery)

The charge and discharge test was conducted as in Example 6, except that the organic sulfur material (PAN-S) obtained in Comparative Example 1 was used as a cathode active material. FIG. 7 shows the charge and discharge characteristics. The initial discharge capacity was 640 mAh/g, which conforms well with the results disclosed in NPL 3, and which is lower than the value obtained in Examples 6 to 8.

Example 9

1-Nonanol (Non-Aqueous Electrolyte Lithium Secondary Battery)

An organic sulfur material was produced as in Example 1, except that 1-nonanol was used as a linear or branched alcohol. Specifically, 20.6486 g of sulfur and 5 mL (0.827 g) of 1-nonanol (Aldrich, purity: 98%) were placed in an alumina Tammann tube (produced by Nikkato, alumina SSA-S, outer diameter: 51 mm, inner diameter: 42 mm, length: 400 mm), and heated to a sample temperature of 350° C. in an electric furnace under nitrogen gas stream (50 mL/min). Then, nonanol was added in 1-mL increments, and the resulting mixture was left for about 15 minutes until the temperature was increased to 350° C., followed by addition of another 1 mL of nonanol, which made the total amount of nonanol additionally added 5 mL. At this time, the solution went up as a vapor to the upper part of the test tube, cooled off at the upper part, and adhered as droplets to the wall of the test tube; thus, 1-nonanol, which is a carbon source, was confirmed to be refluxing as a liquid. Thereafter, the temperature was increased to 439° C., the electric furnace was turned off, and the temperature was maintained at 300° C. or higher for 60 minutes (380° C. or higher for 10 minutes). After cooling, the obtained crude product was heated at 300° C. under nitrogen stream for 2 hours to vaporize and remove the sulfur to thus obtain 2.2769 g of black solid powder (organic sulfur material). Example 9, which involves the starting material addition method, achieved a 10-time increase in yield, compared with those of Examples 1 to 8.

The X-ray diffraction pattern of the obtained sample only showed, as in Example 1, a wide peak at about $2\theta=25°$, which indicates that the sample was an amorphous material. Further, there were no peaks originating from elemental sulfur; thus, the existence of sulfur residue (free sulfur) was not confirmed.

As shown in FIG. 3, the Raman spectrum of the obtained sample showed a main peak at 1440 $cm^{-1}$, as well as peaks at 1900 $cm^{-1}$, 1250 $cm^{-1}$, and 480 $cm^{-1}$. The following are the relations of peak intensities: the peak intensity at 1900 $cm^{-1}$ was about 0.09 times the peak intensity at 1440 $cm^{-1}$, the peak intensity at 1250 $cm^{-1}$ was about 0.35 times the peak intensity at 1440 $cm^{-1}$, and the peak intensity at 480 $cm^{-1}$ was about 0.08 times the peak intensity at 1440 $cm^{-1}$. No peaks were observed in the vicinity of 1066 $cm^{-1}$ or 846 $cm^{-1}$. Further, fitting was performed with respect to 4 components (the $sp^3$ component of the D band (1270 $cm^{-1}$), the $sp^2$ component of the D band (1350 $cm^{-1}$), the $sp^3$ component of the G band (1440 $cm^{-1}$), and the $sp^2$ component of the G band (1590 $cm^{-1}$)) of the spectrum from 1000 to 2000 $cm^{-1}$, which relates to carbon components. As a result, as shown in FIG. 4, the population of the $sp^3$ component of the G band was 69%.

Further, as shown in FIG. 5, the XAFS spectrum showed a main absorption peak at 2473 eV, as well as absorption peaks at 2469 eV and 2472 eV. The following are the relations of peak intensities: the peak intensity at 2469 eV was about 0.10 times the peak intensity at 2473 eV, and the peak intensity at 2472 eV was about 0.69 times the peak intensity at 2473 eV.

According to elemental analysis using the combustion method, the carbon content was 36.3 wt %, the sulfur content was 60.6 wt %, the hydrogen content was 0.3 wt %, and the oxygen and nitrogen were below the detection limit (less than 0.01 wt %).

Figure 8:
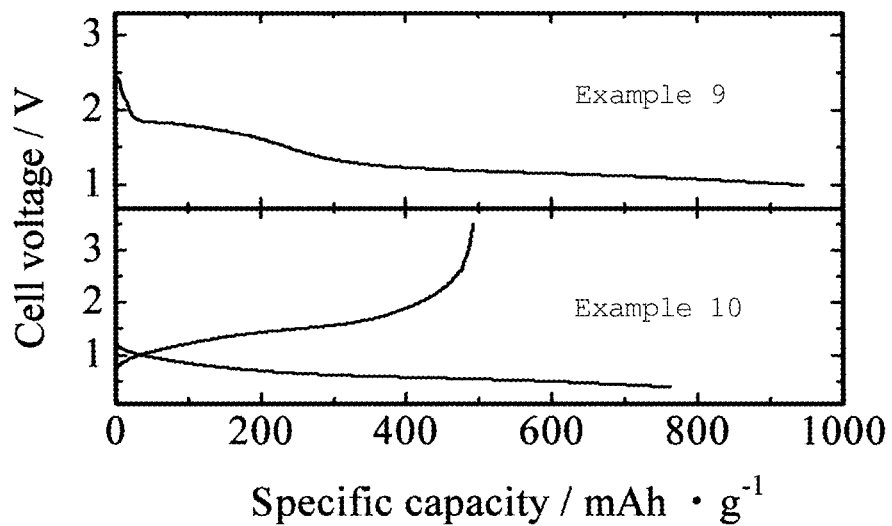
FIG. 8 is a graph showing the charge-and-discharge test results of the non-aqueous electrolyte lithium secondary battery obtained in Example 9 and the all-solid-state lithium-ion secondary battery obtained in Example 10.

The charge and discharge test was conducted in completely the same manner as in Example 1, except that this organic sulfur material was used as a cathode active material of a non-aqueous electrolyte lithium secondary battery. FIG. 8 shows the charge and discharge characteristics. The initial discharge capacity was 940 mAh/g, which was higher than that of the organic sulfur material obtained using polyacrylonitrile (PAN) as a starting material (Comparative Example 1; 630 mAh/g).

The results indicate that the production of an organic sulfur material under the conditions adopted in the present invention and use of the material as a cathode active material of a non-aqueous electrolyte lithium secondary battery led the non-aqueous electrolyte lithium secondary battery to have a high capacity.

Example 10

1-Nonanol (All-Solid-State Lithium-ion Secondary Battery)

The charge and discharge test was conducted as in Example 6, except that the organic sulfur material obtained in Example 9 was used as a cathode active material. FIG. 8 shows the charge and discharge characteristics. The initial discharge capacity was 760 mAh/g, which was higher than that of the organic sulfur material obtained using polyacrylonitrile (PAN) as a starting material (Comparative Example 2; 640 mAh/g). Further, the discharge capacity after 10 cycles was about 320 mAh/g (capacity retention: 42%), demonstrating a relatively excellent reversible cycle.

The results indicate that the production of an organic sulfur material under the conditions adopted in the present invention and use of the material as a cathode active material of an all-solid-state lithium-ion secondary battery led the all-solid-state lithium-ion secondary battery to have a high capacity and excellent reversible cycle characteristics.

Example 11

1-Heptanoic Acid (Non-Aqueous Electrolyte Lithium Secondary Battery)

An organic sulfur material was produced as in Example 1, except that 1-heptanoic acid, which is one kind of linear or branched carboxylic acid, was used in place of 1-octanol, which is one kind of linear or branched alcohol. Specifically, 4.6228 g of sulfur and 2 mL of 1-heptanoic acid (Wako Pure Chemical Industries, Ltd., purity: 98%) were placed in a test tube, and heated to a sample temperature of 457° C. in an electric furnace under nitrogen gas stream (50 mL/min). At this time, the solution went up as a vapor to the upper part of the test tube, cooled off at the upper part, and adhered as droplets to the wall of the test tube; thus, 1-heptanoic acid, which is a carbon source, was confirmed to be refluxing as a liquid. Then, after heating was stopped, the temperature was maintained at 300° C. or higher for 30 minutes (at 380° C. or higher for 10 minutes). The temperature was lowered to room temperature, and the obtained reaction product was heated under nitrogen stream at 300° C. for 2 hours to vaporize and remove the sulfur to thus obtain 0.1688 g of black solid powder (organic sulfur material).

The X-ray diffraction pattern of the obtained sample only showed, as in Example 1, a wide peak at about $2\theta=25°$, which indicates that the sample was an amorphous material. Further, there were no peaks originating from elemental sulfur; thus, the existence of sulfur residue (free sulfur) was not confirmed.

Figure 9:
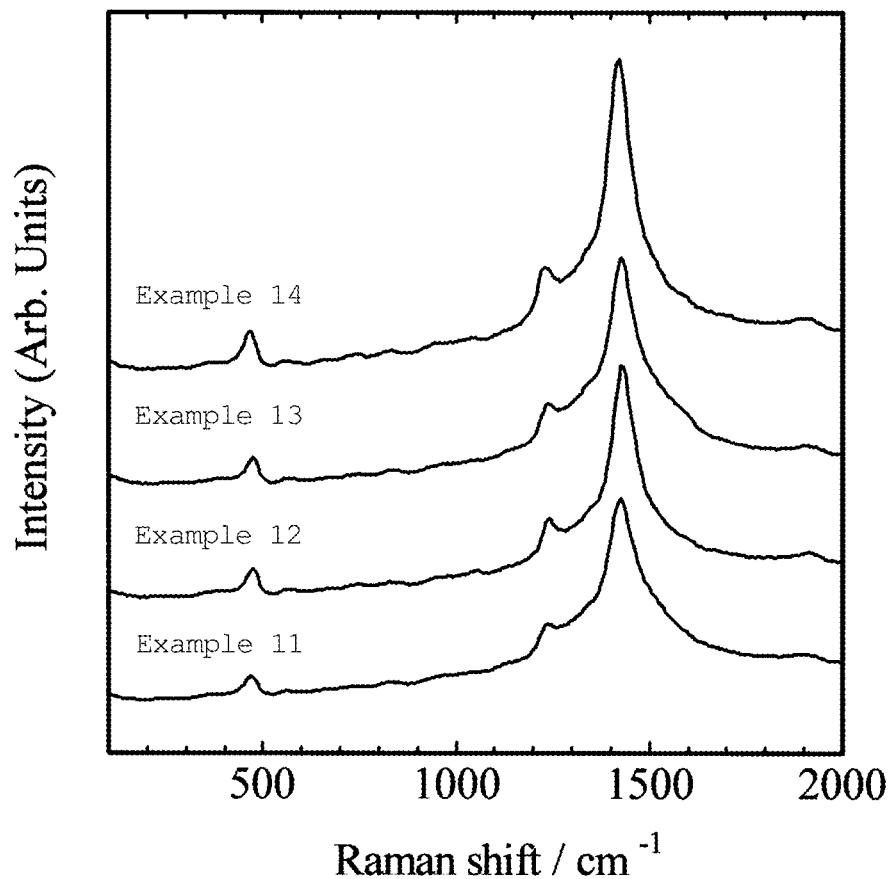
FIG. 9 is a graph showing Raman spectra (100-2000 cm$^{-1}$) of the organic sulfur materials obtained in Examples 11 to 14.
Figure 10:
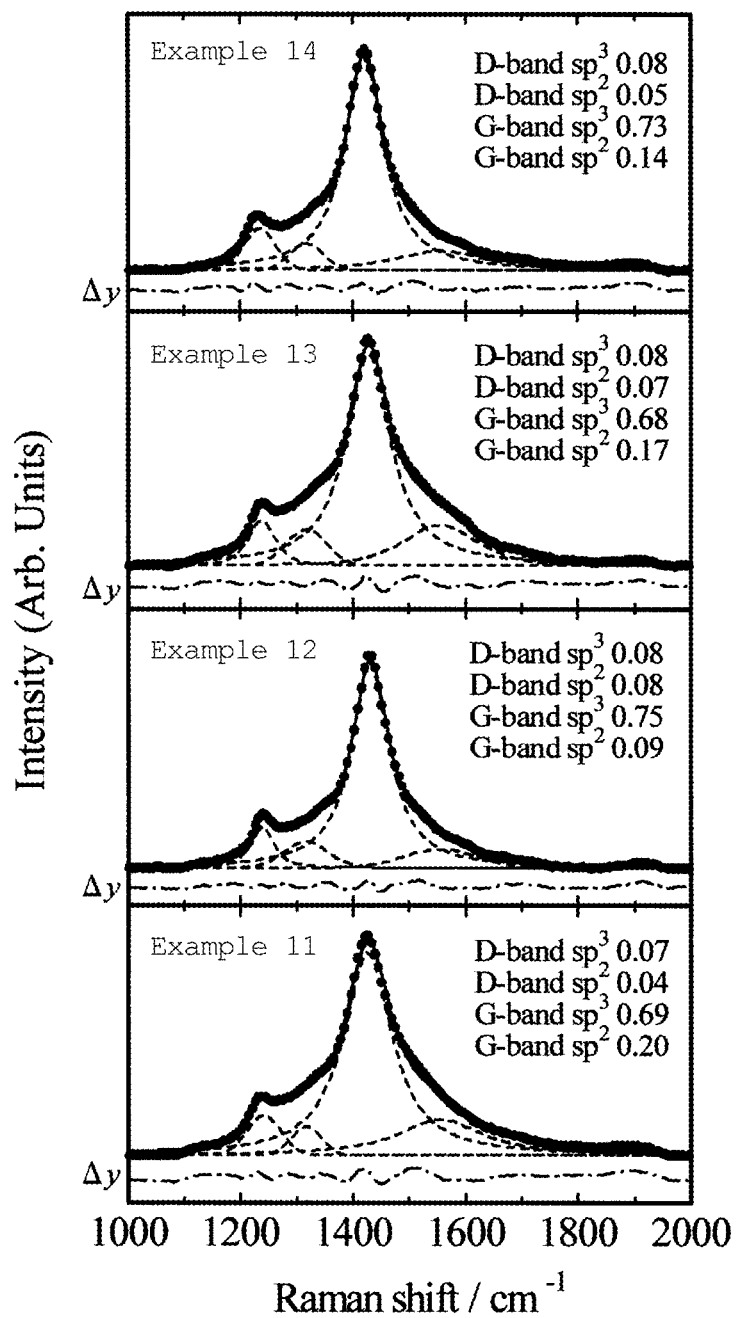
FIG. 10 is a graph showing the results of fitting of four components in the Raman spectrum (1000-2000 cm$^{-1}$) of each organic sulfur material obtained in Examples 11 to 14.

As shown in FIG. 9, the Raman spectrum of the obtained sample showed a main peak at 1440 $cm^{-1}$, as well as peaks at 1900 $cm^{-1}$, 1250 $cm^{-1}$, and 480 $cm^{-1}$. The following are the relations of peak intensities: the peak intensity at 1900 $cm^{-1}$ was about 0.10 times the peak intensity at 1440 $cm^{-1}$, the peak intensity at 1250 $cm^{-1}$ was about 0.31 times the peak intensity at 1440 $cm^{-1}$, and the peak intensity at 480 $cm^{-1}$ was about 0.10 times the peak intensity at 1440 $cm^{-1}$. No peaks were observed in the vicinity of 1066 $cm^{-1}$ or 846 $cm^{-1}$. Further, fitting was performed with respect to 4 components (the $sp^3$ component of the D band (1270 $cm^{-1}$), the $sp^2$ component of the D band (1350 $cm^{-1}$), the $sp^3$ component of the G band (1440 $cm^{-1}$), and the $sp^2$ component of the G band (1590 $cm^{-1}$)) of the spectrum from 1000 to 2000 $cm^{-1}$, which relates to carbon components. As a result, as shown in FIG. 10, the population of the $sp^3$ component of the G band was 69%.

Figure 11:
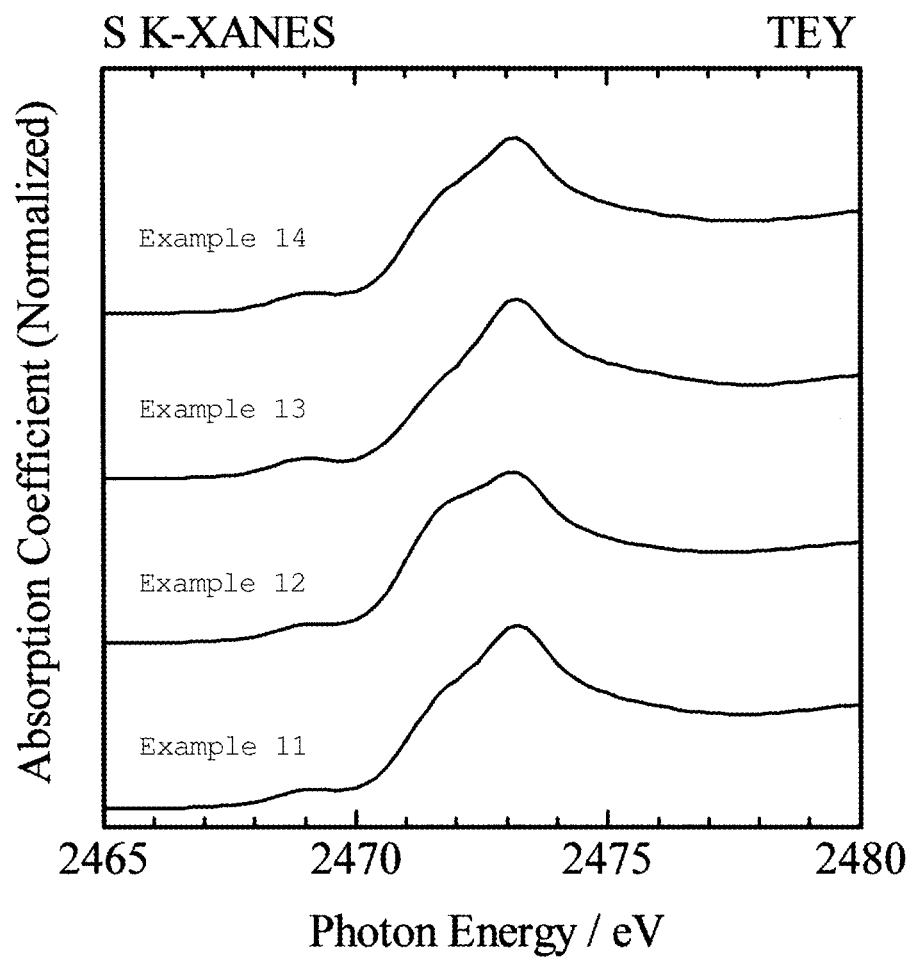
FIG. 11 is a graph showing X-ray absorption fine structure (XAFS) spectra of the organic sulfur materials obtained in Examples 11 to 14 (2465-2480 eV).

Further, as shown in FIG. 11, the XAFS spectrum showed a main absorption peak at 2473 eV, as well as absorption peaks at 2469 eV and 2472 eV. The following are the relations of peak intensities: the peak intensity at 2469 eV was about 0.11 times the peak intensity at 2473 eV, and the peak intensity at 2472 eV was about 0.70 times the peak intensity at 2473 eV.

According to elemental analysis by using the combustion method, the carbon content was 35.9 wt %, the sulfur content was 63.7 wt %, the hydrogen content was 0.2 wt %, and the oxygen and nitrogen were below the detection limit (less than 0.01 wt %).

Accordingly, an organic sulfur material was obtained, which contained carbonized components, e.g., a graphene skeleton, and contained a carbon-sulfur bond.

Figure 12:
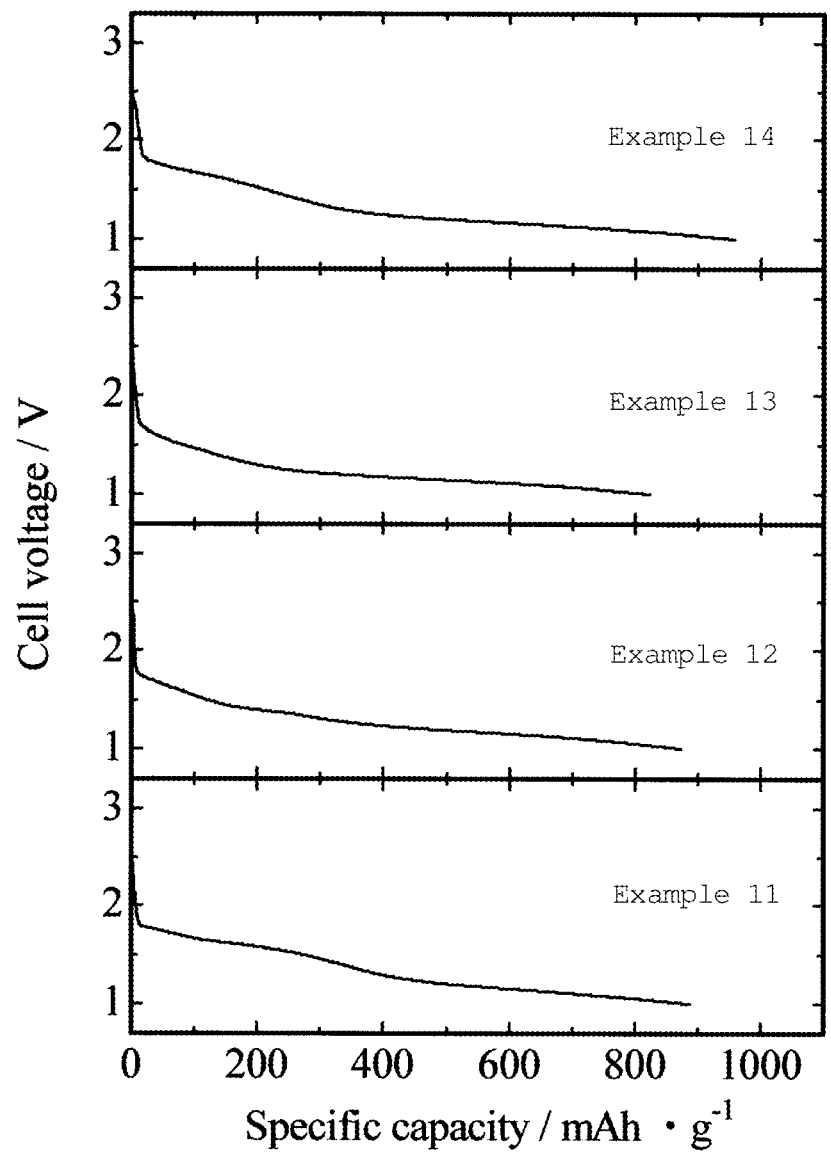
FIG. 12 is a graph showing the charge-and-discharge test results of the non-aqueous electrolyte lithium-ion secondary battery obtained in Examples 11 to 14.

The charge and discharge test was conducted in completely the same manner as in Example 1, except that this organic sulfur material was used as a cathode active material of a non-aqueous electrolyte lithium secondary battery. FIG. 12 shows the charge and discharge characteristics. The initial discharge capacity was 890 mAh/g, which was higher than that of the organic sulfur material obtained using polyacrylonitrile (PAN) as a starting material (Comparative Example 1; 630 mAh/g).

The results indicate that the production of an organic sulfur material under the conditions adopted in the present invention and use of the material as a cathode active material of a non-aqueous electrolyte lithium secondary battery led the non-aqueous electrolyte lithium secondary battery to have a high capacity.

Example 12

1-Octanoic Acid (Non-Aqueous Electrolyte Lithium Secondary Battery)

An organic sulfur material was produced as in Example 1, except that 1-octanoic acid, which is one kind of linear or branched carboxylic acid, was used in place of 1-octanol, which is one kind of linear or branched alcohol. Specifically, 33.1401 g of sulfur and 19.1818 g of 1-octanoic acid (Wako Pure Chemical Industries, Ltd., purity: 97%) were placed in a test tube, and heated to a sample temperature of 350° C. in an electric furnace under nitrogen gas stream (50 mL/min). At this time, the solution went up as a vapor to the upper part of the test tube, cooled off at the upper part, and adhered as droplets to the wall of the test tube; thus, 1-octanoic acid, which is a carbon source, was confirmed to be refluxing as a liquid. Subsequently, heating was stopped, and the temperature was maintained at 300° C. or higher for 30 minutes. The temperature was lowered to room temperature, and the obtained reaction product was heated under nitrogen stream at 350° C. for 2 hours to vaporize and remove the sulfur to thus obtain 0.8339 g of black solid powder (organic sulfur material).

The X-ray diffraction pattern of the obtained sample only showed, as in Example 1, a wide peak at about $2\theta=25°$, which indicates that the sample was an amorphous material. Further, there were no peaks originating from elemental sulfur; thus, the existence of sulfur residue (free sulfur) was not confirmed.

As shown in FIG. 9, the Raman spectrum of the obtained sample showed a main peak at 1440 $cm^{-1}$, as well as peaks at 1900 $cm^{-1}$, 1250 $cm^{-1}$, and 480 $cm^{-1}$. The following are the relations of peak intensities: the peak intensity at 1900 $cm^{-1}$ was about 0.08 times the peak intensity at 1440 $cm^{-1}$, the peak intensity at 1250 $cm^{-1}$ was about 0.28 times the peak intensity at 1440 $cm^{-1}$, and the peak intensity at 480 $cm^{-1}$ was about 0.12 times the peak intensity at 1440 $cm^{-1}$. No peaks were observed in the vicinity of 1066 $cm^{-1}$ or 846 $cm^{-1}$. Further, fitting was performed with respect to 4 components (the $sp^3$ component of the D band (1270 $cm^{-1}$), the $sp^2$ component of the D band (1350 $cm^{-1}$), the $sp^3$ component of the G band (1440 $cm^{-1}$), and the $sp^2$ component of the G band (1590 $cm^{-1}$)) of the spectrum from 1000 to 2000 $cm^{-1}$, which relates to carbon components. As a result, as shown in FIG. 10, the population of the $sp^3$ component of the G band was 75%.

Further, as shown in FIG. 11, the XAFS spectrum showed a main absorption peak at 2473 eV, as well as absorption peaks at 2469 eV and 2472 eV. The following are the relations of peak intensities: the peak intensity at 2469 eV was about 0.12 times the peak intensity at 2473 eV, and the peak intensity at 2472 eV was about 0.86 times the peak intensity at 2473 eV.

According to elemental analysis using the combustion method, the carbon content was 33.2 wt %, the sulfur content was 58.9 wt %, the hydrogen content was 0.4 wt %, and the oxygen and nitrogen were below the detection limit (less than 0.01 wt %).

Accordingly, an organic sulfur material was obtained, which contained carbonized components, e.g., a graphene skeleton, and contained a carbon-sulfur bond.

The charge and discharge test was conducted in completely the same manner as in Example 1, except that this organic sulfur material was used as a cathode active material of a non-aqueous electrolyte lithium secondary battery. FIG. 12 shows the charge and discharge characteristics. The initial discharge capacity was 870 mAh/g, which was higher than that of the organic sulfur material obtained using polyacrylonitrile (PAN) as a starting material (Comparative Example 1; 630 mAh/g).

The results indicate that the production of an organic sulfur material under the conditions adopted in the present invention and use of the material as a cathode active material of a non-aqueous electrolyte lithium secondary battery led the non-aqueous electrolyte lithium secondary battery to have a high capacity.

Example 13

1-Nonanoic Acid (Non-Aqueous Electrolyte Lithium Secondary Battery)

An organic sulfur material was produced as in Example 1, except that 1-nonanoic acid, which is one kind of linear or branched carboxylic acid, was used in place of 1-octanol, which is one kind of linear or branched alcohol. Specifically, 5.7955 g of sulfur and 2.6677 g of 1-nonanoic acid (Wako Pure Chemical Industries, Ltd., purity 90%) were placed in a test tube, and heated to a sample temperature of 429° C. in an electric furnace under nitrogen gas stream (50 mL/min). At this time, the solution went up as a vapor to the upper part of the test tube, cooled off at the upper part, and adhered as droplets to the wall of the test tube; thus, 1-nonanoic acid, which is a carbon source, was confirmed to be refluxing as a liquid. Then, after heating was stopped, the temperature was maintained at 300° C. or higher for 30 minutes (at 380° C. or higher for 8 minutes). The temperature was lowered to room temperature, and the obtained reaction product was heated under nitrogen stream at 300° C. for 2 hours to vaporize and remove the sulfur to thus obtain 0.2638 g of black solid powder (organic sulfur material).

The X-ray diffraction pattern of the obtained sample only showed, as in Example 1, a wide peak at about 2θ=25°, which indicates that the sample was an amorphous material. Further, there were no peaks originating from elemental sulfur; thus, the existence of sulfur residue (free sulfur) was not confirmed.

As shown in FIG. 9, the Raman spectrum of the obtained sample showed a main peak at 1440 $cm^{-1}$, as well as peaks at 1900 $cm^{-1}$, 1250 $cm^{-1}$, and 480 $cm^{-1}$. The following are the relations of peak intensities: the peak intensity at 1900 $cm^{-1}$ was about 0.06 times the peak intensity at 1440 $cm^{-1}$, the peak intensity at 1250 $cm^{-1}$ was about 0.31 times the peak intensity at 1440 $cm^{-1}$, and the peak intensity at 480 $cm^{-1}$ was about 0.11 times the peak intensity at 1440 $cm^{-1}$. No peaks were observed in the vicinity of 1066 $cm^{-1}$ or 846 $cm^{-1}$. Further, fitting was performed with respect to 4 components (the $sp^3$ component of the D band (1270 $cm^{-1}$), the $sp^2$ component of the D band (1350 $cm^{-1}$), the $sp^3$ component of the G band (1440 $cm^{-1}$), and the $sp^2$ component of the G band (1590 $cm^{-1}$)) of the spectrum from 1000 to 2000 $cm^{-1}$, which relates to carbon components. As a result, as shown in FIG. 10, the population of the $sp^3$ component of the G band was 68%.

Further, as shown in FIG. 11, the XAFS spectrum showed a main absorption peak at 2473 eV, as well as absorption peaks at 2469 eV and 2472 eV. The following are the relations of peak intensities: the peak intensity at 2469 eV was about 0.13 times the peak intensity at 2473 eV, and the peak intensity at 2472 eV was about 0.63 times the peak intensity at 2473 eV.

According to elemental analysis using the combustion method, the carbon content was 37.9 wt %, the sulfur content was 61.7 wt %, the hydrogen content was 0.2 wt %, and the oxygen and nitrogen were below the detection limit (less than 0.01 wt %).

Accordingly, an organic sulfur material was obtained, which contained carbonized components, e.g., a graphene skeleton, and contained a carbon-sulfur bond.

The charge and discharge test was conducted in completely the same manner as in Example 1, except that this organic sulfur material was used as a cathode active material of a non-aqueous electrolyte lithium secondary battery. FIG. 12 shows the charge and discharge characteristics. The initial discharge capacity was 820 mAh/g, which was higher than that of the organic sulfur material obtained using polyacrylonitrile (PAN) as a starting material (Comparative Example 1; 630 mAh/g).

The results indicate that the production of an organic sulfur material under the conditions adopted in the present invention and use of the material as a cathode active material of a non-aqueous electrolyte lithium secondary battery led the non-aqueous electrolyte lithium secondary battery to have a high capacity.

Example 14

1-Decanoic Acid (Non-Aqueous Electrolyte Lithium Secondary Battery)

An organic sulfur material was produced as in Example 1, except that 1-decanoic acid, which is one kind of linear or branched carboxylic acid, was used in place of 1-octanol, which is one kind of linear or branched alcohol. Specifically, 5.8511 g of sulfur and 1.1972 g of 1-decanoic acid (Wako Pure Chemical Industries, Ltd., purity: 98%) were placed in a test tube, and heated to a sample temperature of 452° C. in an electric furnace under nitrogen gas stream (50 mL/min). At this time, the solution went up as a vapor to the upper part of the test tube, cooled off at the upper part, and adhered as droplets to the wall of the test tube; thus, 1-decanoic acid, which is a carbon source, was confirmed to be refluxing as a liquid. Then, after heating was stopped, the temperature was maintained at 300° C. or higher for 30 minutes (at 380° C. or higher for 10 minutes). The temperature was lowered to room temperature, and the obtained reaction product was heated under nitrogen stream at 300° C. for 2 hours to vaporize and remove the sulfur to thus obtain 0.7402 g of black solid powder (organic sulfur material).

The X-ray diffraction pattern of the obtained sample only showed, as in Example 1, a wide peak at about 2θ=25°, which indicates that the sample was an amorphous material. Further, there were no peaks originating from elemental sulfur; thus, the existence of sulfur residue (free sulfur) was not confirmed.

As shown in FIG. 9, the Raman spectrum of the obtained sample showed a main peak at 1440 $cm^{-1}$, as well as peaks at 1900 $cm^{-1}$, 1250 $cm^{-1}$, and 480 $cm^{-1}$. The following are the relations of peak intensities: the peak intensity at 1900 $cm^{-1}$ was about 0.06 times the peak intensity at 1440 $cm^{-1}$; the peak intensity at 1250 $cm^{-1}$ was about 0.28 times the peak intensity at 1440 $cm^{-1}$; and the peak intensity at 480 $cm^{-1}$ was about 0.11 times the peak intensity at 1440 $cm^{-1}$. No peaks were observed in the vicinity of 1066 $cm^{-1}$ or 846 $cm^{-1}$. Further, fitting was performed with respect to 4 components (the sp³ component of the D band (1270 cm⁻¹), the sp² component of the D band (1350 cm⁻¹), the sp³ component of the G band (1440 cm⁻¹), and the sp² component of the G band (1590 cm⁻¹)) of the spectrum from 1000 to 2000 cm⁻¹, which relates to carbon components. As a result, as shown in FIG. 10, the population of the sp³ component of the G band was 73%.

Further, as shown in FIG. 11, the XAFS spectrum showed a main absorption peak at 2473 eV, as well as absorption peaks at 2469 eV and 2472 eV. The following are the relations of peak intensities: the peak intensity at 2469 eV was about 0.13 times the peak intensity at 2473 eV, and the peak intensity at 2472 eV was about 0.75 times the peak intensity at 2473 eV.

According to elemental analysis using the combustion method, the carbon content was 35.9 wt %, the sulfur content was 63.6 wt %, the hydrogen content was 0.2 wt %, and the oxygen and nitrogen were below the detection limit (less than 0.01 wt %).

Accordingly, an organic sulfur material was obtained, which contained carbonized components, e.g., a graphene skeleton, and contained a carbon-sulfur bond.

The charge and discharge test was conducted in completely the same manner as in Example 1, except that this organic sulfur material was used as a cathode active material of a non-aqueous electrolyte lithium secondary battery. FIG. 12 shows the charge and discharge characteristics. The initial discharge capacity was 960 mAh/g, which was higher than that of the organic sulfur material obtained using polyacrylonitrile (PAN) as a starting material (Comparative Example 1; 630 mAh/g).

The results indicate that the production of an organic sulfur material under the conditions adopted in the present invention and use of the material as a cathode active material of a non-aqueous electrolyte lithium secondary battery led the non-aqueous electrolyte lithium secondary battery to have a high capacity.

Example 15

1-Heptanoic Acid (All-Solid-State Lithium-ion Secondary Battery)

Figure 13:
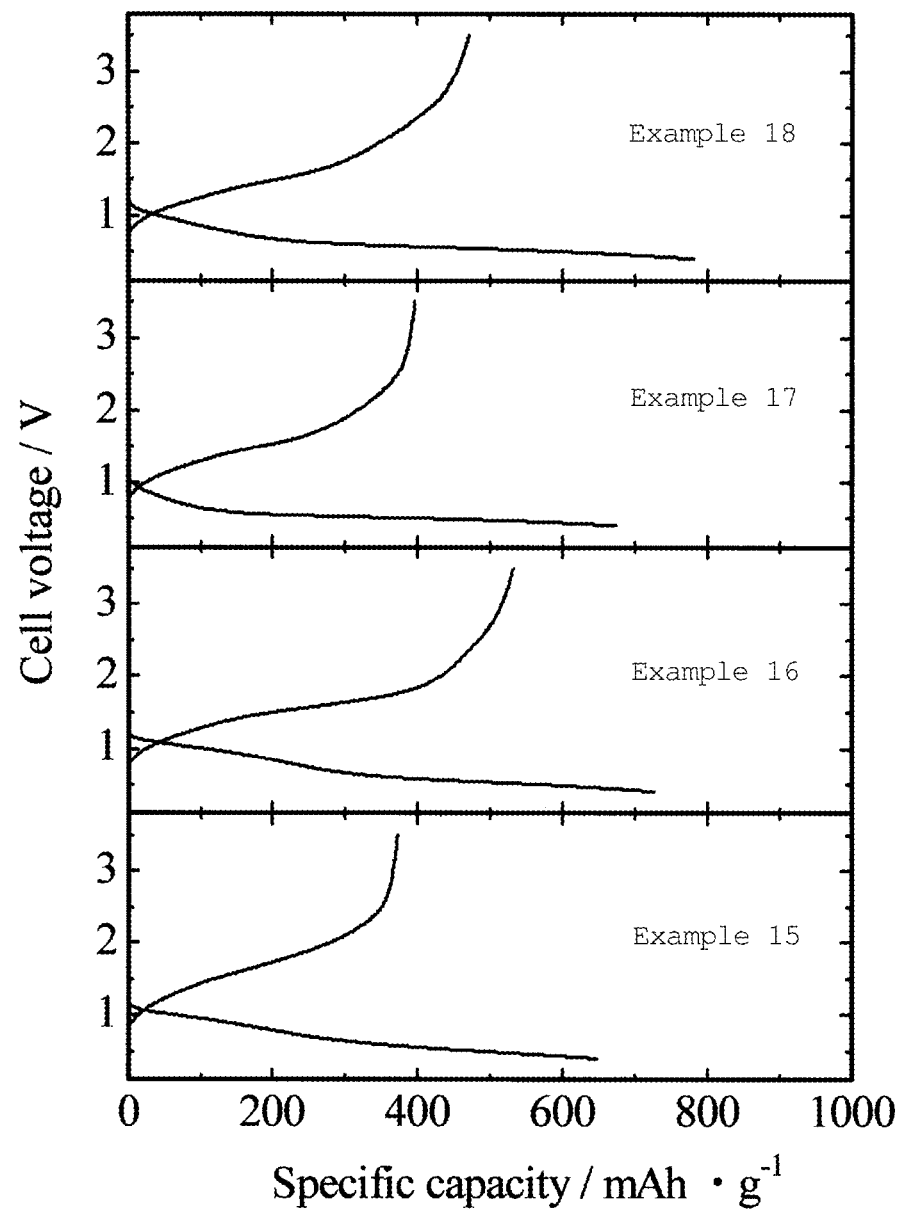
FIG. 13 is a graph showing the charge-and-discharge test results of the all-solid-state lithium-ion secondary batteries obtained in Examples 15 to 18.

The charge and discharge test was conducted as in Example 6, except that the organic sulfur material obtained in Example 11 was used as a cathode active material. FIG. 13 shows the charge and discharge characteristics. The initial discharge capacity was 650 mAh/g, which was higher than that of the organic sulfur material obtained using polyacrylonitrile (PAN) as a starting material (Comparative Example 2; 640 mAh/g). Further, the discharge capacity after 10 cycles was about 160 mAh/g (capacity retention: 25%), demonstrating a relatively excellent reversible cycle.

The results indicate that the production of an organic sulfur material under the conditions adopted in the present invention and use of the material as a cathode active material of an all-solid-state lithium-ion secondary battery led the all-solid-state lithium-ion secondary battery to have a high capacity and excellent reversible cycle characteristics.

Example 16

1-Octanoic Acid (All-Solid-State Lithium-ion Secondary Battery)

The charge and discharge test was conducted as in Example 6, except that the organic sulfur material obtained in Example 12 was used as a cathode active material. FIG. 13 shows the charge and discharge characteristics. The initial discharge capacity was 730 mAh/g, which was higher than that of the organic sulfur material obtained using polyacrylonitrile (PAN) as a starting material (Comparative Example 2; 640 mAh/g). Further, the discharge capacity after 10 cycles was about 300 mAh/g (capacity retention: 41%), demonstrating a relatively excellent reversible cycle.

The results indicate that the production of an organic sulfur material under the conditions adopted in the present invention and use of the material as a cathode active material of an all-solid-state lithium-ion secondary battery led the all-solid-state lithium-ion secondary battery to have a high capacity and excellent reversible cycle characteristics.

Example 17

1-Nonanoic Acid (All-Solid-State Lithium-ion Secondary Battery)

The charge and discharge test was conducted as in Example 6, except that the organic sulfur material obtained in Example 13 was used as a cathode active material. FIG. 13 shows the charge and discharge characteristics. The initial discharge capacity was 670 mAh/g, which was higher than that of the organic sulfur material obtained using polyacrylonitrile (PAN) as a starting material (Comparative Example 2; 640 mAh/g). Further, the discharge capacity after 10 cycles was about 180 mAh/g (capacity retention: 26%), demonstrating a relatively excellent reversible cycle.

The results indicate that the production of an organic sulfur material under the conditions adopted in the present invention and use of the material as a cathode active material of an all-solid-state lithium-ion secondary battery led the all-solid-state lithium-ion secondary battery to have a high capacity and excellent reversible cycle characteristics.

Example 18

1-Decanoic Acid (All-Solid-State Lithium-ion Secondary Battery)

The charge and discharge test was conducted as in Example 6, except that the organic sulfur material obtained in Example 14 was used as a cathode active material. FIG. 13 shows the charge and discharge characteristics. The initial discharge capacity was 780 mAh/g, which was higher than that of the organic sulfur material obtained using polyacrylonitrile (PAN) as a starting material (Comparative Example 2; 640 mAh/g). Further, the discharge capacity after 10 cycles was about 120 mAh/g (capacity retention: 16%), demonstrating a relatively excellent reversible cycle.

The results indicate that the production of an organic sulfur material under the conditions adopted in the present invention and use of the material as a cathode active material of an all-solid-state lithium-ion secondary battery led the all-solid-state lithium-ion secondary battery to have a high capacity and excellent reversible cycle characteristics.

As shown in the above results, the organic sulfur material produced by a desired method by using a linear or branched alcohol, or a linear or branched carboxylic acid, as a starting material had desired properties, and this organic sulfur material was suitably applied to a non-aqueous electrolyte lithium secondary battery or all-solid-state lithium-ion secondary battery that exhibits a high capacity. Further, the use of an alcohol as a starting material, or the use of a carboxylic acid, which is an alcohol oxide, as a starting material, both yielded an organic sulfur material with the same properties. This suggests that the use of an aldehyde, which is also an alcohol oxide, as a starting material, would also yield an organic sulfur material with the same properties.

The invention claimed is:

1. A sulfur material comprising carbon, hydrogen, sulfur, oxygen, and nitrogen as constituent elements, and having a peak of 2473±0.5 eV in an S K-edge X-ray absorption fine structure spectrum, the peak being of highest intensity in the spectrum, wherein the sulfur material has a carbon content of 30 to 45 wt %, a sulfur content of 55 to 70 wt %, a hydrogen content of 0.01 to 1 wt %, an oxygen content of 0.01 to 1 wt %, and a nitrogen content of 0.01 to 1 wt %.

2. A method for producing a sulfur material comprising carbon, hydrogen, sulfur, oxygen, and nitrogen as constituent elements, and having a peak of 2473±0.5 eV in an S K-edge X-ray absorption fine structure spectrum, the peak being of highest intensity in the spectrum and the sulfur material having a carbon content of 30 to 45 wt %, a sulfur content of 55 to 70 wt %, a hydrogen content of 0.01 to 1 wt %, an oxygen content of 0.01 to 1 wt %, and a nitrogen content of 0.01 to 1 wt %,
the method comprising the step of subjecting a solution containing a sulfur-containing starting material and at least one member selected from the group consisting of linear or branched alcohols, linear or branched carboxylic acids, and linear or branched aldehydes to heat treatment in an inert atmosphere.

3. The production method according to claim 2, wherein the heat treatment step comprises refluxing at 300 to 600° C. the solution containing a sulfur-containing starting material and at least one member selected from the group consisting of linear or branched alcohols, linear or branched carboxylic acids, and linear or branched aldehydes.

4. The production method according to claim 2, wherein the method comprises the step of performing heating at 250 to 350° C. under an inert gas stream after the heat treatment step.

5. An electrode active material for a battery, the material comprising the sulfur material of claim 1.

6. An electrode active material for a battery, the material comprising the sulfur material obtained by the production method of claim 2.

7. The electrode active material for a battery according to claim 5, which is an electrode active material for a lithium-ion secondary battery.

8. A battery comprising, as a constituent element, the electrode active material for a battery of claim 5.

9. The battery according to claim 8, which is a lithium-ion secondary battery.

10. An all-solid-state lithium-ion secondary battery comprising, as constituent elements, the electrode active material for a battery of claim 5, and a lithium-ion conductive solid electrolyte.

11. The all-solid-state lithium-ion secondary battery according to claim 10, wherein the lithium-ion conductive solid electrolyte contains a sulfide-based solid electrolyte.

12. The sulfur material according to claim 1, further having a peak selected from the group consisting of 2469±0.5 eV and 2472±0.5 eV in an S K-edge X-ray absorption fine structure spectrum.

13. The sulfur material according to claim 1, further having peaks of 480±50 $cm^{-1}$, 1250±50 $cm^{-1}$, 1440±50 $cm^{-1}$, and 1900±50 $cm^{-1}$ in a Raman spectrum detected by Raman spectroscopy, the peak of 1440±50 $cm^{-1}$ having the highest intensity in the Raman spectrum.

14. The sulfur material according to claim 13, wherein the intensities of the Raman scattering peaks of 480±50 $cm^{-1}$, 1250±50 $cm^{-1}$, and 1900±50 $cm^{-1}$ are each 0.5 times, or less, the intensity of the Raman scattering peak of 1440±50 $cm^{-1}$.

15. The sulfur material according to claim 13, having no Raman scattering peak of 846±50 $cm^{-1}$ or 1066±50 $cm^{-1}$ in the Raman spectrum detected by Raman spectroscopy.

16. The sulfur material according to claim 13, wherein a population of a component having a peak of Raman scattering intensity of 1440±50 $cm^{-1}$ is 50% or more when fitting is performed with respect to four components having peaks of Raman scattering intensity of 1270±50 $cm^{-1}$, 1350±50 $cm^{-1}$, 1440±50 $cm^{-1}$, and 1590±50 $cm^{-1}$ in the Raman spectrum within a range of 1000 to 2000 $cm^{-1}$ detected by Raman spectroscopy.

* * * * *